US008802398B2

(12) United States Patent
Mikkelsen et al.

(10) Patent No.: US 8,802,398 B2
(45) Date of Patent: Aug. 12, 2014

(54) OXIDATION PROCESS

(75) Inventors: Jorn Dalgaard Mikkelsen, Hvidovre (DK); Karsten Matthias Kragh, Viby J (DK); Rene Mikkelsen, Brabrand (DK); Patrick Maria Franciscus Derkx, Tikøb (DK); Shukun Yu, Malmoe (SE); Harm Mulder, Oegstgeest (NL); Igor Nikolaev, Noordwijk (NL)

(73) Assignee: Dupont Nutrition Biosciences Aps, Copenhagen (DK)

( * ) Notice: Subject to any disclaimer, the term of this patent is extended or adjusted under 35 U.S.C. 154(b) by 209 days.

(21) Appl. No.: 12/915,853

(22) Filed: Oct. 29, 2010

(65) Prior Publication Data

US 2011/0236935 A1 Sep. 29, 2011

Related U.S. Application Data

(63) Continuation-in-part of application No. PCT/IB2009/005738, filed on Apr. 30, 2009.

(30) Foreign Application Priority Data

Apr. 30, 2008 (GB) .................................. 0807881.8
Apr. 30, 2008 (GB) .................................. 0807882.6
Jun. 25, 2008 (GB) .................................. 0811662.6
Sep. 17, 2008 (GB) .................................. 0817077.1

(51) Int. Cl.
*C12P 19/04* (2006.01)
*C12P 19/10* (2006.01)
*C12P 19/00* (2006.01)
*C12N 1/21* (2006.01)
*C12N 15/63* (2006.01)

(52) U.S. Cl.
USPC ............ 435/100; 435/101; 435/102; 435/190

(58) Field of Classification Search
None
See application file for complete search history.

(56) References Cited

U.S. PATENT DOCUMENTS

| | | | |
|---|---|---|---|
| 4,663,448 A | 5/1987 | Chiu | |
| 4,675,394 A | 6/1987 | Solarek et al. | |
| 6,265,570 B1 | 7/2001 | Cimecioglu et al. | |
| 2003/0150573 A1 | 8/2003 | Anderson et al. | |
| 2003/0228672 A1* | 12/2003 | Choi et al. ..................... | 435/189 |
| 2006/0198819 A1 | 9/2006 | Behrens et al. | |

FOREIGN PATENT DOCUMENTS

| | | |
|---|---|---|
| JP | 2003159079 | 6/2003 |
| WO | WO 99/23240 | 5/1999 |

OTHER PUBLICATIONS

Chica et al. Curr Opin Biotechnol. Aug. 2005; 16(4):378-84.*
Witkowski et al. Biochemistry. Sep. 7, 1999; 38(36): 11643-50.*
Seffernick et al. J Bacteriol. Apr. 2001; 183 (8): 2405-10.*
Ec 1.1.1.1, Alcohol Dehydrogenase, (created 1961) IUBMB Biochemical Nomenclature, wvvw.chem.qmul.ac.uk/iubmb/enzyme/EC1/1/1/1.html.
Ec 1.1.1.2, Alcohol Dehydrogenase (NADP+), (created 1961) IUBMB Biochemical Nomenclature, www.chem.qmul.ac.uk/iubmb/enzyme/EC1/1/1/2.html.
Ec 1.1.5.2, Quinoprotein Glucose Dehydrogenase (created 1982 as 1.1.99.17), IUBMB Biochemical Nomenclature, www.chem.qmul.ac.uk/iubmb/enzyme/EC1/1/5/2.html.
JPO Proteins Host, Dec. 16, 2003, Alcohol/Aldehyde Dehydrogenase, Production Method Thereof and Use Thereof, JP 2003-159079: ID: BD681475.
JPO Proteins Host, Apr. 26, 2005, Enzymatic Method for the Enantioselective Reduction of Keto Compounds, JP2004-527251: ID: BD787481.
Uniprot Accession No. A7ZJQ4_ECO24, (Oct. 23, 2007).
Osao Adachi, et al., Purification and Characterization of Particulate Alcohol Dehydrogenase . . . , Agric. Biol. Chem. (1978) vol. 42, No. 11, p. 2045-2056.
Osao Adachi, et al., Purification and Properties of Particulate Alcohol Dehydrogenase . . . , Agric. Biol. Chem. (1978) vol. 42, No. 12, p. 2331-2340.
Osao Adachi, et al., Purification and Properties of Methanol Dehydrogenase and Aldehyde . . . , Agric. Biol. Chem. (1990) vol. 54, No. 12, p. 3123-3129.
Stephen F. Altschul, et al., Basic Local Alignment Search Tool, J. Mol. Biol. (1990) vol. 215, p. 403-410.
George Buchi, et al., A Synthesis of Methoxatin, J. American Chemical Society (1985) vol. 107, p. 5555-5556.
M.O. Dayhoff, et al., A Model of Evolutionary Change in Proteins, Atlas of Protein Sequence and Structure (1978) vol. 5, Sup. 3, p. 345-352, Natl. Biomed. Res. Found. Wash. DC.
Gaston H. Gonnet, et al., Exhaustive Matching of the Entire Protein Sequence Database, Science (1992) vol. 256, p. 1443-1445.
Steven Henikoff, et al., Amino Acid Substitution Matrices From Protein Blocks, PNAS USA (1992) vol. 89, p. 10915-10919.
Desmond G. Higgins, et al., Clustal: A Package for Performing Multiple Sequence Alignment . . . , Gene (1988) vol. 73, p. 237-244.
Desmond G. Higgins, et al., Clustal V: Improved Software for Multiple Sequence Alignment, CABIOS (1992) vol. 8, No. 2, p. 189-191.
David C. Horwell, The 'Peptoid' Approach to the Design of Non-Peptide, Small Molecule Agonists . . . , TIBTECH (1995) vol. 13, p. 132-134.

(Continued)

*Primary Examiner* — Tekchand Saidha
*Assistant Examiner* — MD. Younus Meah
(74) *Attorney, Agent, or Firm* — Vedder Price P.C.; Thomas J. Kowalski

(57) ABSTRACT

A method of oxidizing a saccharide, by contacting the saccharide with an alcohol dehydrogenase (ADH) enzyme selected from a quinone redox cofactor-dependent ADH, a nicotinamide adenine dinucleotide (NAD$^+$) redox cofactor-dependent ADH, a nicotinamide adenine dinucleotide phosphate (NADP$^+$) redox cofactor-dependent ADH, and any combination thereof is described. An oxidized saccharide obtainable by the method and products, in particular food products and paper products, containing the oxidized saccharide, are also described.

43 Claims, 4 Drawing Sheets

(56) References Cited

OTHER PUBLICATIONS

Toshihiro Ishiguro, et al., Synthesis of Branched Cyclomaltooligosaccharide . . . , Carbohydrate Research (2001) vol. 331, p. 423-430.

David T. Jones, et al., The Rapid Generation of Mutation Data Matrices From Protein Sequences, CABIOS (1992) vol. 8, No. 3, p. 275-282.

Takeshi Kumazawa, et al., Levels of Pyrroloquinoline Quinone in Various Foods, Biochem. J. (1995) vol. 307, p. 331-333.

M.A. Larkin, et al., Clustal W and Clustal X version 2.0, Bioinformatics (2007) vol. 23, No. 21, p. 2947-2948.

Kazunobu Matsushita, et al., Membrane-bound D-Glucose Dehydrogenase From *Pseudomonas* sp.: . . . , Agric. Biol. Chem. (1980) vol. 44, No. 7, p. 1505-1512.

Emiko Shinagawa, et al., Purification and Characterization of D-Sorbitol Dehydrogenase . . . , Agric. Biol. Chem. (1982) vol. 46, No. 1, p. 135-141.

Takashi Shibata, et al., Purification and Molecular Characterization of a Quinoprotein . . . , J. of Bioscience and Bioengineering (2001) vol. 92, No. 6, p. 524-531.

Reyna J. Simon, et al., Peptoids: A Modular Approach to Drug Discovery, PNAS USA (1992) vol. 89, p. 9367-9371.

Teruhide Sugisawa, et al., Isolation and Characterization of Membrane-bound L-sorbose Dehydrogenase . . . , Agric. Biol. Chem. (1991) vol. 55, No. 2, p. 363-370.

Julie D. Thompson, et al., Clustal W: Improving the Sensitivity of Progressive Multiple Sequence Alignment . . . , Nucleic Acids Research (1994) vol. 22, No. 22, p. 4673-4680.

Hirohide Toyama, et al., Quinohemoprotein Alcohol Dehydrogenases: Structure, Function . . . , Archives of Biochemistry and Biophysics (2004) vol. 428, p. 10-21.

\* cited by examiner 2,3,4,5,6-Pentahydroxy-hexanal O-ethyl-oxime $C_8H_{17}NNaO_6^+$
Exact Mass: 246.09481

$C_{10}H_{20}N_2NaO_6^+$
Exact Mass: 287.12136

SEQUENCE LISTING

<160> NUMBER OF SEQ ID NOS: 10

<210> SEQ ID NO 1
<211> LENGTH: 608
<212> TYPE: PRT
<213> ORGANISM: Pseudogluconobacter saccharoketogenes

<400> SEQUENCE: 1

```
Met Arg Phe Glu Tyr Leu Arg Gln Asn Val Val Gly Leu Ala Leu Ser
1               5                   10                  15

Thr Ala Leu Ile Ala Ser Leu Ser Gly Pro Ala Phe Ala Gln His Asp
                20                  25                  30

Ala Asn Ala Ala Ala Glu Pro Ser Lys Ala Gly Gln Ser Ala Ile Glu
            35                  40                  45

Asn Phe Gln Pro Val Thr Ala Asp Asp Leu Ala Gly Lys Asn Pro Ala
        50                  55                  60

Asn Trp Pro Ile Leu Arg Gly Asn Tyr Gln Gly Trp Gly Tyr Ser Pro
65                  70                  75                  80

Leu Asp Gln Ile Asn Lys Asp Asn Val Gly Asp Leu Gln Leu Val Trp
                85                  90                  95

Ser Arg Thr Met Glu Pro Gly Ser Asn Glu Gly Ala Ala Ile Ala Tyr
            100                 105                 110

Asn Gly Val Ile Phe Leu Gly Asn Thr Asn Asp Val Ile Gln Ala Ile
        115                 120                 125

Asp Gly Lys Thr Gly Ser Leu Ile Trp Glu Tyr Arg Arg Lys Leu Pro
    130                 135                 140

Ser Ala Ser Lys Phe Ile Asn Ser Leu Gly Ala Ala Lys Arg Ser Ile
145                 150                 155                 160

Ala Leu Phe Gly Asp Lys Val Tyr Phe Val Ser Trp Asp Asn Phe Val
                165                 170                 175

Val Ala Leu Asp Ala Lys Thr Gly Lys Leu Ala Trp Glu Thr Asn Arg
            180                 185                 190

Gly Gln Gly Val Glu Glu Gly Val Ala Asn Ser Ser Gly Pro Ile Val
        195                 200                 205

Val Asp Gly Val Val Ile Ala Gly Ser Thr Cys Gln Phe Ser Gly Phe
    210                 215                 220

Gly Cys Tyr Val Thr Gly Thr Asp Ala Glu Ser Gly Glu Glu Leu Trp
225                 230                 235                 240

Arg Asn Thr Phe Ile Pro Arg Pro Gly Glu Glu Gly Asp Asp Thr Trp
                245                 250                 255

Gly Gly Ala Pro Tyr Glu Asn Arg Trp Met Thr Gly Ala Trp Gly Gln
            260                 265                 270

Ile Thr Tyr Asp Pro Glu Leu Asp Leu Val Tyr Tyr Gly Ser Thr Gly
        275                 280                 285

Ala Gly Pro Ala Ser Glu Val Gln Arg Gly Thr Glu Gly Gly Thr Leu
    290                 295                 300

Ala Gly Thr Asn Thr Arg Phe Ala Val Lys Pro Lys Thr Gly Glu Val
305                 310                 315                 320

Val Trp Lys His Gln Thr Leu Pro Arg Asp Asn Trp Asp Ser Glu Cys
                325                 330                 335

Thr Phe Glu Met Met Val Val Ser Thr Ser Val Asn Pro Asp Ala Lys
            340                 345                 350

Ala Asp Gly Met Met Ser Val Gly Ala Asn Val Pro Arg Gly Glu Thr
        355                 360                 365
```

Arg Lys Val Leu Thr Gly Val Pro Cys Lys Thr Gly Val Ala Trp Gln
    370             375                 380

Phe Asp Ala Lys Thr Gly Asp Tyr Phe Trp Ser Lys Ala Thr Val Glu
385             390                 395                 400

Gln Asn Ser Ile Ala Ser Ile Asp Asp Thr Gly Leu Val Thr Val Asn
                405                 410                 415

Glu Asp Met Ile Leu Lys Glu Pro Gly Lys Thr Tyr Asn Tyr Cys Pro
            420                 425                 430

Thr Phe Leu Gly Gly Arg Asp Trp Pro Ser Ala Gly Tyr Leu Pro Lys
        435                 440                 445

Ser Asn Leu Tyr Val Ile Pro Leu Ser Asn Ala Cys Tyr Asp Val Met
    450                 455                 460

Ala Arg Thr Thr Glu Ala Thr Pro Ala Asp Val Tyr Asn Thr Asp Ala
465             470                 475                 480

Thr Leu Val Leu Ala Pro Gly Lys Thr Asn Met Gly Arg Val Asp Ala
                485                 490                 495

Ile Asp Leu Ala Thr Gly Glu Thr Lys Trp Ser Tyr Glu Thr Arg Ala
            500                 505                 510

Ala Leu Tyr Asp Pro Val Leu Thr Thr Gly Gly Asp Leu Val Phe Val
        515                 520                 525

Gly Gly Ile Asp Arg Asp Phe Arg Ala Leu Asp Ala Glu Ser Gly Lys
    530                 535                 540

Glu Val Trp Ser Thr Arg Leu Pro Gly Ala Val Ser Gly Tyr Thr Thr
545             550                 555                 560

Ser Tyr Ser Ile Asp Gly Arg Gln Tyr Val Ala Val Ser Gly Gly
                565                 570                 575

Ser Leu Gly Gly Pro Thr Phe Gly Pro Thr Thr Pro Asp Val Asp Ser
        580                 585                 590

Ala Ser Gly Ala Asn Gly Ile Tyr Val Phe Ala Leu Pro Glu Lys Lys
    595                 600                 605

<210> SEQ ID NO 2
<211> LENGTH: 252
<212> TYPE: PRT
<213> ORGANISM: Lactobacillus kefir

<400> SEQUENCE: 2

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
                20                  25                  30

Lys Val Val Ile Thr Gly Arg His Ala Asp Val Gly Glu Lys Ala Ala
            35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65              70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

```
Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
            165                 170                 175

Lys Asp Tyr Asp Val Arg Val Asn Thr Val His Pro Gly Tyr Ile Lys
        180                 185                 190

Thr Pro Leu Val Asp Asp Leu Glu Gly Ala Glu Glu Met Met Ser Gln
    195                 200                 205

Arg Thr Lys Thr Pro Met Gly His Ile Gly Glu Pro Asn Asp Ile Ala
210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 3
<211> LENGTH: 386
<212> TYPE: PRT
<213> ORGANISM: Saccharomyces cerevisiae

<400> SEQUENCE: 3

```
Met Ser Ala Ala Thr Val Gly Lys Pro Ile Lys Cys Ile Ala Ala Val
1               5                   10                  15

Ala Tyr Asp Ala Lys Lys Pro Leu Ser Val Glu Ile Thr Val Asp
            20                  25                  30

Ala Pro Lys Ala His Glu Val Arg Ile Lys Ile Glu Tyr Thr Ala Val
        35                  40                  45

Cys His Thr Asp Ala Tyr Thr Leu Ser Gly Ser Asp Pro Glu Gly Leu
    50                  55                  60

Phe Pro Cys Val Leu Gly His Glu Gly Ala Gly Ile Val Glu Ser Val
65                  70                  75                  80

Gly Asp Asp Val Ile Thr Val Lys Pro Gly Asp His Val Ile Ala Leu
                85                  90                  95

Tyr Thr Ala Glu Cys Gly Lys Cys Lys Phe Cys Thr Ser Gly Lys Thr
            100                 105                 110

Asn Leu Cys Gly Ala Val Arg Ala Thr Gln Gly Lys Gly Val Met Pro
        115                 120                 125

Asp Gly Thr Thr Arg Phe His Asn Ala Lys Gly Glu Asp Ile Tyr His
    130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
            180                 185                 190

Asn Val Gln Lys Gly Asp Thr Val Ala Val Phe Gly Cys Gly Thr Val
        195                 200                 205

Gly Leu Ser Val Ile Gln Gly Ala Lys Leu Arg Gly Ala Ser Lys Ile
    210                 215                 220

Ile Ala Ile Asp Ile Asn Asn Lys Lys Gln Tyr Cys Ser Gln Phe
225                 230                 235                 240

Gly Ala Thr Asp Phe Val Asn Pro Lys Glu Asp Leu Ala Lys Asp Gln
                245                 250                 255

Thr Ile Val Glu Lys Leu Ile Glu Met Thr Asp Gly Gly Leu Asp Phe
```

```
            260                 265                 270
Thr Phe Asp Cys Thr Gly Asn Thr Lys Ile Met Arg Asp Ala Leu Glu
            275                 280                 285

Ala Cys His Lys Gly Trp Gly Gln Ser Ile Ile Ile Gly Val Ala Ala
            290                 295                 300

Ala Gly Glu Glu Ile Ser Thr Arg Pro Phe Gln Leu Val Thr Gly Arg
305                 310                 315                 320

Val Trp Lys Gly Ser Ala Phe Gly Gly Ile Lys Gly Arg Ser Glu Met
            325                 330                 335

Gly Gly Leu Ile Lys Asp Tyr Gln Lys Gly Ala Leu Lys Val Glu Glu
            340                 345                 350

Phe Ile Thr His Arg Arg Pro Phe Lys Glu Ile Asn Gln Ala Phe Glu
            355                 360                 365

Asp Leu His Asn Gly Asp Cys Leu Arg Thr Val Leu Lys Ser Asp Glu
            370                 375                 380

Ile Lys
385

<210> SEQ ID NO 4
<211> LENGTH: 352
<212> TYPE: PRT
<213> ORGANISM: Thermoanaerobium brockii

<400> SEQUENCE: 4

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
            35                  40                  45

Ile Gly Glu Arg His Asn Met Ile Leu Gly His Glu Ala Val Gly Glu
        50                  55                  60

Val Val Glu Val Gly Ser Glu Val Lys Asp Phe Lys Pro Gly Asp Arg
65              70                  75                  80

Val Val Val Pro Ala Ile Thr Pro Asp Trp Arg Thr Ser Glu Val Gln
            85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
            115                 120                 125

Ala Asp Met Asn Leu Ala His Leu Pro Lys Glu Ile Pro Leu Glu Ala
        130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
            165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
            195                 200                 205

Tyr Tyr Gly Ala Thr Asp Ile Val Asn Tyr Lys Asp Gly Pro Ile Glu
        210                 215                 220

Ser Gln Ile Met Asn Leu Thr Glu Gly Lys Gly Val Asp Ala Ala Ile
225                 230                 235                 240
```

```
Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350

<210> SEQ ID NO 5
<211> LENGTH: 371
<212> TYPE: PRT
<213> ORGANISM: Escherichia coli

<400> SEQUENCE: 5

Met His Arg Gln Ser Phe Phe Leu Val Pro Leu Ile Cys Leu Ser Ser
1               5                   10                  15

Ala Leu Trp Ala Ala Pro Ala Thr Val Asn Val Glu Val Leu Gln Asp
            20                  25                  30

Lys Leu Asp His Pro Trp Ala Leu Ala Phe Leu Pro Asp Asn His Gly
        35                  40                  45

Met Leu Ile Thr Leu Arg Gly Gly Glu Leu Arg His Trp Gln Ala Gly
    50                  55                  60

Lys Gly Leu Ser Ala Pro Leu Ser Gly Val Pro Asp Val Trp Ala His
65                  70                  75                  80

Gly Gln Gly Gly Leu Leu Asp Val Val Leu Ala Pro Asp Phe Ala Gln
                85                  90                  95

Ser Arg Arg Ile Trp Leu Ser Tyr Ser Glu Val Gly Asp Asp Gly Lys
            100                 105                 110

Ala Gly Thr Ala Val Gly Tyr Gly Arg Leu Ser Asp Asp Leu Ser Lys
        115                 120                 125

Val Thr Asp Phe Arg Thr Val Phe Arg Gln Met Pro Lys Leu Ser Thr
    130                 135                 140

Gly Asn His Phe Gly Gly Arg Leu Val Phe Asp Gly Lys Gly Tyr Leu
145                 150                 155                 160

Phe Ile Ala Leu Gly Glu Asn Asn Gln Arg Pro Thr Ala Gln Asp Leu
                165                 170                 175

Asp Lys Leu Gln Gly Lys Leu Val Arg Leu Thr Asp Gln Gly Glu Ile
            180                 185                 190

Pro Asp Asp Asn Pro Phe Ile Lys Glu Ser Gly Ala Arg Ala Glu Ile
        195                 200                 205

Trp Ser Tyr Gly Ile Arg Asn Pro Gln Gly Met Ala Met Asn Pro Trp
    210                 215                 220

Ser Asn Ala Leu Trp Leu Asn Glu His Gly Pro Arg Gly Gly Asp Glu
225                 230                 235                 240

Ile Asn Ile Pro Gln Lys Gly Lys Asn Tyr Gly Trp Pro Leu Ala Thr
                245                 250                 255

Trp Gly Ile Asn Tyr Ser Gly Phe Lys Ile Pro Glu Ala Lys Gly Glu
            260                 265                 270
```

Ile Val Ala Gly Thr Glu Gln Pro Val Phe Tyr Trp Lys Asp Ser Pro
    275                 280                 285

Ala Val Ser Gly Met Ala Phe Tyr Asn Ser Asp Lys Phe Pro Gln Trp
    290                 295                 300

Gln Gln Lys Leu Phe Ile Gly Ala Leu Lys Lys Asp Val Ile Val
305                 310                 315                 320

Met Ser Val Asn Gly Asp Lys Val Thr Glu Asp Gly Arg Ile Leu Thr
                325                 330                 335

Asp Arg Gly Gln Arg Ile Arg Asp Val Arg Thr Gly Pro Asp Gly Tyr
                340                 345                 350

Leu Tyr Val Leu Thr Asp Glu Ser Ser Gly Glu Leu Leu Lys Val Ser
    355                 360                 365

Pro Arg Asn
    370

<210> SEQ ID NO 6
<211> LENGTH: 1894
<212> TYPE: DNA
<213> ORGANISM: Artificial Sequence
<220> FEATURE:
<223> OTHER INFORMATION: Codon optimized PQQ-ADH gene

<400> SEQUENCE: 6

```
ggtaccacaa gtttgtacaa aaaagcaggc ttcatgagat cgagtacct gcgccagaac      60
gttgtcggtt tggctctttc taccgccctg atcgcatccc tcagcggccc tgcttttgcc    120
caacacgacg ctaatgctgc cgccgaacca tcaaaggcag acagtcggc aattgagaac     180
ttccaaccgg tgactgctga cgatttggcc ggtaaaaacc ctgcaaattg cccatcctt     240
cgtggcaact accagggatg ggggtatagt ccactggacc agattaacaa ggataatgtc    300
ggtgatttgc agctcgtttg gtctcggaca atggaaccgg aagcaatga gggcgctgct    360
atcgcctata cggtgtgat ttttctgggc aacacgaatg acgttatcca agccattgat    420
ggaaaaaccg gttccttat ctgggaatac agacgaaagc tcccctcagc atctaaattc    480
attaactcgt tggggggctgc taagaggtcc atcgccctgt ttggcgacaa ggtctacttc    540
gtgagttggg ataattttgt tgtcgcccctt gacgcaaaga ctggaaaact ggcttgggag    600
acaaacagag tcaaggtgt tgaggaaggc gtggccaact ctagcggacc tattgttgtc    660
gatggcgtcg tgatcgcagg gtccacctgc cagttctcag gttttggctg ttatgtgact    720
ggaacggacg ctgagtcggg tgaagaattg tggcgcaata ccttcattcc acgtccggga    780
gaggaaggtg acgatacatg gggcggagca ccttacgaga accggtggat gacgggtgcc    840
tggggccaaa tcacctatga cccagaactt gatctcgttt actatggttc tactgggggct    900
ggacctgcct ccgaggtcca gagaggtaca gaaggcggca ccctggctgg aactaataca    960
cgctttgccg tgaagcccaa aacgggagag gttgtctgga acatcaaaac cttgccgaga   1020
gacaactggg atagcgagtg cactttcgaa atgatggttg tctcaaccag tgtgaatcca   1080
gacgctaagg cagatggtat gatgtctgtt ggggccaacg tgcctagggg cgagacacgt   1140
aaggttctca cggtgtcccc gtgtaaaaact ggcgtggctt ggcagtttga tgcaaagacg   1200
ggagactact tctggtcgaa agccaccgtc gaacaaaaact ccatcgctag cattgacgat   1260
accggtctgg ttacagtcaa tgaggacatg attttgaaag aacccggcaa gacttacaac   1320
tattgcccaa cattccttgg agggcgagat tggccttctg ccggttacct gccgaagtca   1380
aatttgtatg tgatcccact ctccaacgca tgttacgatg ttatggctag aaccactgag   1440
```

```
gccacgcccg ctgacgtcta taacaccgat gccacactgg tgcttgcacc tggcaagacg   1500
aatatgggac gcgttgacgc tatcgatctc gccaccggtg aaacaaaatg gtcgtacgag   1560
acaagagctg cactgtatga cccggtcttg accactggcg agatcttgt ttttgtgggt    1620 ggaattgacc gtgacttccg ggctctggat gccgagagcg ggaaagaagt ctggtctaca    1680
aggttgccag gtgcagtgtc cggctacacc acgtcataca gtattgatgg cagacagtat   1740
gttgccgtcg tttctggtgg tagcctcggc ggacctacct ttggaccgac tacacccgac   1800
gtggattccg cttcgggagc aaacgggatc tacgtctttg ccctgcctga aagaagtaa    1860 taaacccagc tttcttgtac aaagtggtga gctc                               1894
```

<210> SEQ ID NO 7
<211> LENGTH: 572
<212> TYPE: PRT
<213> ORGANISM: Pseudogluconobacter saccharoketogenes

<400> SEQUENCE: 7

```
Ala Glu Pro Ser Lys Ala Gly Gln Ser Ala Ile Glu Asn Phe Gln Pro
1               5                   10                  15

Val Thr Ala Asp Asp Leu Ala Gly Lys Asn Pro Ala Asn Trp Pro Ile
            20                  25                  30

Leu Arg Gly Asn Tyr Gln Gly Trp Gly Tyr Ser Pro Leu Asp Gln Ile
        35                  40                  45

Asn Lys Asp Asn Val Gly Asp Leu Gln Leu Val Trp Ser Arg Thr Met
    50                  55                  60

Glu Pro Gly Ser Asn Glu Gly Ala Ala Ile Ala Tyr Asn Gly Val Ile
65                  70                  75                  80

Phe Leu Gly Asn Thr Asn Asp Val Ile Gln Ala Ile Asp Gly Lys Thr
                85                  90                  95

Gly Ser Leu Ile Trp Glu Tyr Arg Arg Lys Leu Pro Ser Ala Ser Lys
            100                 105                 110

Phe Ile Asn Ser Leu Gly Ala Ala Lys Arg Ser Ile Ala Leu Phe Gly
        115                 120                 125

Asp Lys Val Tyr Phe Val Ser Trp Asp Asn Phe Val Val Ala Leu Asp
    130                 135                 140

Ala Lys Thr Gly Lys Leu Ala Trp Glu Thr Asn Arg Gly Gln Gly Val
145                 150                 155                 160

Glu Glu Gly Val Ala Asn Ser Ser Gly Pro Ile Val Val Asp Gly Val
                165                 170                 175

Val Ile Ala Gly Ser Thr Cys Gln Phe Ser Gly Phe Gly Cys Tyr Val
            180                 185                 190

Thr Gly Thr Asp Ala Glu Ser Gly Glu Glu Leu Trp Arg Asn Thr Phe
        195                 200                 205

Ile Pro Arg Pro Gly Glu Glu Gly Asp Asp Thr Trp Gly Ala Pro
    210                 215                 220

Tyr Glu Asn Arg Trp Met Thr Gly Ala Trp Gln Ile Thr Tyr Asp
225                 230                 235                 240

Pro Glu Leu Asp Leu Val Tyr Tyr Gly Ser Thr Gly Ala Gly Pro Ala
                245                 250                 255

Ser Glu Val Gln Arg Gly Thr Glu Gly Gly Thr Leu Ala Gly Thr Asn
            260                 265                 270

Thr Arg Phe Ala Val Lys Pro Lys Thr Gly Glu Val Val Trp Lys His
        275                 280                 285
```

```
Gln Thr Leu Pro Arg Asp Asn Trp Asp Ser Glu Cys Thr Phe Glu Met
    290                 295                 300
Met Val Val Ser Thr Ser Val Asn Pro Asp Ala Lys Ala Asp Gly Met
305                 310                 315                 320
Met Ser Val Gly Ala Asn Val Pro Arg Gly Glu Thr Arg Lys Val Leu
                325                 330                 335
Thr Gly Val Pro Cys Lys Thr Gly Val Ala Trp Gln Phe Asp Ala Lys
            340                 345                 350
Thr Gly Asp Tyr Phe Trp Ser Lys Ala Thr Val Glu Gln Asn Ser Ile
        355                 360                 365
Ala Ser Ile Asp Asp Thr Gly Leu Val Thr Val Asn Glu Asp Met Ile
370                 375                 380
Leu Lys Glu Pro Gly Lys Thr Tyr Asn Tyr Cys Pro Thr Phe Leu Gly
385                 390                 395                 400
Gly Arg Asp Trp Pro Ser Ala Gly Tyr Leu Pro Lys Ser Asn Leu Tyr
                405                 410                 415
Val Ile Pro Leu Ser Asn Ala Cys Tyr Asp Val Met Ala Arg Thr Thr
            420                 425                 430
Glu Ala Thr Pro Ala Asp Val Tyr Asn Thr Asp Ala Thr Leu Val Leu
        435                 440                 445
Ala Pro Gly Lys Thr Asn Met Gly Arg Val Asp Ala Ile Asp Leu Ala
450                 455                 460
Thr Gly Glu Thr Lys Trp Ser Tyr Glu Thr Arg Ala Ala Leu Tyr Asp
465                 470                 475                 480
Pro Val Leu Thr Thr Gly Gly Asp Leu Val Phe Val Gly Gly Ile Asp
                485                 490                 495
Arg Asp Phe Arg Ala Leu Asp Ala Glu Ser Gly Lys Glu Val Trp Ser
            500                 505                 510
Thr Arg Leu Pro Gly Ala Val Ser Gly Tyr Thr Thr Ser Tyr Ser Ile
        515                 520                 525
Asp Gly Arg Gln Tyr Val Ala Val Val Ser Gly Gly Ser Leu Gly Gly
530                 535                 540
Pro Thr Phe Gly Pro Thr Thr Pro Asp Val Asp Ser Ala Ser Gly Ala
545                 550                 555                 560
Asn Gly Ile Tyr Val Phe Ala Leu Pro Glu Lys Lys
                565                 570

<210> SEQ ID NO 8
<211> LENGTH: 228
<212> TYPE: PRT
<213> ORGANISM: Lactobacillus kefir

<400> SEQUENCE: 8

Asp Lys Phe Val Glu Glu Gly Ala Lys Val Val Ile Thr Gly Arg His
1               5                   10                  15
Ala Asp Val Gly Glu Lys Ala Ala Lys Ser Ile Gly Gly Thr Asp Val
                20                  25                  30
Ile Arg Phe Val Gln His Asp Ala Ser Asp Glu Ala Gly Trp Thr Lys
            35                  40                  45
Leu Phe Asp Thr Thr Glu Glu Ala Phe Gly Pro Val Thr Thr Val Val
        50                  55                  60
Asn Asn Ala Gly Ile Ala Val Ser Lys Ser Val Glu Asp Thr Thr Thr
65                  70                  75                  80
Glu Glu Trp Arg Lys Leu Leu Ser Val Asn Leu Asp Gly Val Phe Phe
                85                  90                  95
```

-continued

```
Gly Thr Arg Leu Gly Ile Gln Arg Met Lys Asn Lys Gly Leu Gly Ala
            100                 105                 110

Ser Ile Ile Asn Met Ser Ser Ile Glu Gly Phe Val Gly Asp Pro Thr
        115                 120                 125

Leu Gly Ala Tyr Asn Ala Ser Lys Gly Ala Val Arg Ile Met Ser Lys
    130                 135                 140

Ser Ala Ala Leu Asp Cys Ala Leu Lys Asp Tyr Asp Val Arg Val Asn
145                 150                 155                 160

Thr Val His Pro Gly Tyr Ile Lys Thr Pro Leu Val Asp Asp Leu Glu
                165                 170                 175

Gly Ala Glu Glu Met Met Ser Gln Arg Thr Lys Thr Pro Met Gly His
            180                 185                 190

Ile Gly Glu Pro Asn Asp Ile Ala Trp Ile Cys Val Tyr Leu Ala Ser
        195                 200                 205

Asp Glu Ser Lys Phe Ala Thr Gly Ala Glu Phe Val Val Asp Gly Gly
    210                 215                 220

Tyr Thr Ala Gln
225

<210> SEQ ID NO 9
<211> LENGTH: 351
<212> TYPE: PRT
<213> ORGANISM: Escherichia coli

<400> SEQUENCE: 9

Ala Pro Ala Thr Val Asn Val Glu Val Leu Gln Asp Lys Leu Asp His
1               5                   10                  15

Pro Trp Ala Leu Ala Phe Leu Pro Asp Asn His Gly Met Leu Ile Thr
            20                  25                  30

Leu Arg Gly Gly Glu Leu Arg His Trp Gln Ala Gly Lys Gly Leu Ser
        35                  40                  45

Ala Pro Leu Ser Gly Val Pro Asp Val Trp Ala His Gly Gln Gly Gly
    50                  55                  60

Leu Leu Asp Val Val Leu Ala Pro Asp Phe Ala Gln Ser Arg Arg Ile
65                  70                  75                  80

Trp Leu Ser Tyr Ser Glu Val Gly Asp Asp Gly Lys Ala Gly Thr Ala
                85                  90                  95

Val Gly Tyr Gly Arg Leu Ser Asp Asp Leu Ser Lys Val Thr Asp Phe
            100                 105                 110

Arg Thr Val Phe Arg Gln Met Pro Lys Leu Ser Thr Gly Asn His Phe
        115                 120                 125

Gly Gly Arg Leu Val Phe Asp Gly Lys Gly Tyr Leu Phe Ile Ala Leu
    130                 135                 140

Gly Glu Asn Asn Gln Arg Pro Thr Ala Gln Asp Leu Asp Lys Leu Gln
145                 150                 155                 160

Gly Lys Leu Val Arg Leu Thr Asp Gln Gly Glu Ile Pro Asp Asp Asn
                165                 170                 175

Pro Phe Ile Lys Glu Ser Gly Ala Arg Ala Glu Ile Trp Ser Tyr Gly
            180                 185                 190

Ile Arg Asn Pro Gln Gly Met Ala Met Asn Pro Trp Ser Asn Ala Leu
        195                 200                 205

Trp Leu Asn Glu His Gly Pro Arg Gly Gly Asp Glu Ile Asn Ile Pro
    210                 215                 220

Gln Lys Gly Lys Asn Tyr Gly Trp Pro Leu Ala Thr Trp Gly Ile Asn
```

-continued

```
                225                 230                 235                 240
        Tyr Ser Gly Phe Lys Ile Pro Glu Ala Lys Gly Glu Ile Val Ala Gly
                        245                 250                 255

Thr Glu Gln Pro Val Phe Tyr Trp Lys Asp Ser Pro Ala Val Ser Gly
                        260                 265                 270

Met Ala Phe Tyr Asn Ser Asp Lys Phe Pro Gln Trp Gln Gln Lys Leu
                        275                 280                 285

Phe Ile Gly Ala Leu Lys Asp Lys Asp Val Ile Val Met Ser Val Asn
                        290                 295                 300

Gly Asp Lys Val Thr Glu Asp Gly Arg Ile Leu Thr Asp Arg Gly Gln
        305                 310                 315                 320

Arg Ile Arg Asp Val Arg Thr Gly Pro Asp Gly Tyr Leu Tyr Val Leu
                        325                 330                 335

Thr Asp Glu Ser Ser Gly Glu Leu Leu Lys Val Ser Pro Arg Asn
                        340                 345                 350

<210> SEQ ID NO 10
<211> LENGTH: 10
<212> TYPE: PRT
<213> ORGANISM: Artificial Sequence
<220> FEATURE:
<223> OTHER INFORMATION: Sequence of the N-terminus of the mature PQQ-
      ADH protein

<400> SEQUENCE: 10

Ala Glu Pro Ser Lys Ala Gly Gln Ser Ala
1               5                   10
```

OXIDATION PROCESS

REFERENCE TO RELATED APPLICATIONS

This application is a continuation-in-part application of international patent application Serial No. PCT/IB2009/005738 filed Apr. 30, 2009, which published as PCT Publication No. WO 2009/133464 on Nov. 5, 2009, which claims benefit of United Kingdom patent application No. 0807882.6 filed 30 Apr. 2008, United Kingdom patent application No. 0811662.6 filed 25 Jun. 2008 and U.S. patent application No. 61/099,667 filed 24 Sep. 2008, the contents of each of which are incorporated herein by reference. The present application also claims benefit of United Kingdom patent application No. 0807881.8 filed 30 Apr. 2008 and U.S. patent application No. 61/099,698 filed 24 Sep. 2008, the contents of each of which are incorporated herein by reference. The present application also claims benefit of United Kingdom patent application No. 0817077.1 filed 17 Sep. 2008 and U.S. patent application No. 61/099,715 filed 24 Sep. 2008, the contents of each of which are incorporated herein by reference.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference, and may be employed in the practice of the invention.

FIELD OF THE INVENTION

This invention relates to an oxidation process.

In particular, the present invention relates to a method for modifying polysaccharides.

More particularly, the present invention relates to a method of oxidising polysaccharides, as well as oxidised polysaccharides obtainable by the method and their use in a number of applications, particularly food products and paper products.

BACKGROUND OF THE INVENTION

A number of hydrocolloids, pectin, alginate, carrageenans, potato starch and carboxymethyl cellulose are negatively charged due to galacturonate (Pectin), α-D-mannuronate and α-L-guluronate (Alginate), sulphate groups (carrageenans), phosphate groups (potato starch) and carboxymethyl groups (carboxymethyl-cellulose). These substitutions have a profound influence on the functionality of the hydrocolloids in complex food matrices. Whereas pectin, alginate, potato starch and carrageenan are naturally occurring and are synthesized by plants and algae, carboxymethylcellulose is produced from cellulose by chemical treatment. Due to regulatory restriction and costs for approvals, only a few chemically modified hydrocolloids have been approved for use in foods.

A large number of food and feed products contain starch and therefore may be suitable for further processes like enzymatic modification. In particular, in the bakery process, control of starch retrogradation and recrystallization is of importance in slowing staling of bread.

Polysaccharide derivatives containing aldehyde groups and their use as paper additives are known in the art. For example, U.S. Pat. No. 4,675,394 describes polysaccharide aldehydes, such as starch, gum and cellulose aldehydes and their preparation by a non-oxidative method which involves reacting the polysaccharide base, in the presence of alkali, with a derivatising acetal reagent and then hydrolyzing the resulting acetal.

Oxidized saccharides, in particular oxidized polysaccharides, are useful as coupling agents in various technical fields, in particular in the pharmaceutical industry, where such compounds act to enhance the solubility and delivery of various pharmaceuticals. For example, US2006198819 describes a method for producing a conjugate of a glycoprotein having at least one terminal galactose or derivative thereof, and a protractor group covalently bonded thereto, the method including a step of contacting the galactose-containing glycoprotein with galactose oxidase to oxidise the galactosyll group. The conjugates are stated to have increased in vivo plasma half-life compared to non-conjugated glycoprotein.

U.S. Pat. No. 4,663,448 describes aldehyde-containing heteropolysaccharides, in particular starch ether derivatives, and their preparation using the enzyme galactose oxidase, in which the C-6 position of the glycoside unit is oxidised to the aldehyde functionality.

U.S. Pat. No. 6,265,570 describes stable, sold water soluble starch aldehyde compositions and methods for their preparation by preparing a converted starch acetal and hydrolysis of the acetal under acid conditions to form the starch aldehyde.

Chemical oxidation of polysaccharides such as starch to prepare aldehyde derivatives thereof is known in the art. For example, U.S. Pat. No. 7,247,722 describes preparation of polysaccharide aldehydes using selective oxidation using nitroxyl radical mediator, such as 2,2,6,6-tetramethyl-1-piperidinyloxy (TEMPO) radical.

WO 99/23240 describes a method for producing oxidised starch by using a reagent, such as TEMPO, which produces an oxoammonium ion, in conjunction with an oxidising enzyme, in particular an oxidase (such as laccase) or a peroxidase. However, in the process described in this document, it is the TEMPO which is the oxidising agent: the enzyme is used to regenerate the TEMPO to enable it to be used in catalytic quantities. Chemical oxidations of this type, however, often require harsh reagents and the regiospecificity of such chemical oxidations including the TEMPO method, is limited.

There is therefore a need for an oxidation method for sugars which oxidises alcohol functionalities in sugar molecules more selectively, in particular at the C-6 or C-5 positions of hexose and pentose rings respectively. Furthermore, there is a need for methods for performing such oxidation reactions using milder reagents.

Citation or identification of any document in this application is not an admission that such document is available as prior art to the present invention.

SUMMARY OF THE INVENTION

In a first aspect, the invention comprises a method of oxidising a saccharide, by contacting the saccharide with an alcohol dehydrogenase (ADH) enzyme selected from a quinone redox cofactor-dependent ADH, a nicotinamide adenine dinucleotide ($NAD^+$) redox cofactor-dependent ADH, a nicotinamide adenine dinucleotide phosphate ($NADP^+$) redox cofactor-dependent ADH, and any combination thereof.

In a second aspect, the invention comprises an oxidised saccharide obtained or obtainable by the above method.

In a third aspect, the invention comprises a product containing an oxidised saccharide obtained or obtainable by the above method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Additional Aspects of the Present Invention

The present invention also encompasses methods comprising the use of—as well as the uses of—ADH active polypeptides that are co- or post-translationally processed during expression, for example by signal peptide cleavage. Post-translational cleavage may also occur at the C-terminal. Preferred co- or post-translational processing occurs at the N-terminal end to yield N-terminal truncated sequences.

Therefore in some embodiments of the present invention the effective fragment thereof (also referred to as functional fragment thereof) is the mature polypeptide produced by the native host or a suitable appropriate expression host.

The present invention also encompasses the co- or post-translationally processed ADH active polypeptides.

The present invention also encompasses nucleotide sequences that encode such co- or post-translationally processed active polypeptides.

In addition, the present invention encompasses an amino acid sequence that is expressed from or is expressable from all or part of said nucleotide sequences.

An example of a co- or post-translationally processed active polypeptide is presented as SEQ ID No. 1a.

Without wishing to be bound by theory, SEQ ID No. 2 may be optionally cleaved to SEQ ID No. 2a.

Without wishing to be bound by theory, SEQ ID No. 5 may be optionally cleaved to SEQ ID No. 5a.

Thus, the present invention also encompasses:

An amino acid sequence comprising SEQ ID No. 1A or an amino acid sequence having at least 75% amino acid sequence identity therewith but not SEQ ID No. 1.

An amino acid sequence comprising SEQ ID No. 1A or an amino acid sequence having at least 80%, at least 85%, at least 90%, at least 95%, at least 96%, at least 97%, at least 98% or at least 99%, amino acid sequence identity therewith.

An amino acid sequence comprising SEQ ID No. 2A or an amino acid sequence having at least 75% amino acid sequence identity therewith but not SEQ ID No. 2.

An amino acid sequence comprising SEQ ID No. 2A or an amino acid sequence having at least 80%, at least 85%, at least 90%, at least 95%, at least 96%, at least 97%, at least 98% or at least 99%, amino acid sequence identity therewith.

An amino acid sequence comprising SEQ ID No. 5A or an amino acid sequence having at least 75% amino acid sequence identity therewith but not SEQ ID No. 5.

An amino acid sequence comprising SEQ ID No. 5A or an amino acid sequence having at least 80%, at least 85%, at least 90%, at least 95%, at least 96%, at least 97%, at least 98% or at least 99%, amino acid sequence identity therewith.

A nucleotide sequence encoding any of said amino acid sequences.

A vector comprising said nucleotide sequence.

A host transformed with said nucleotide sequence or said vector.

The host may be a bacterial host, a fungal host, a yeast host or a plant host.

A method comprising expressing said nucleotide sequence or said vector.

Some Preferred Aspects of the Present Invention

Preferred aspects of the present invention are apparent in the description and in the examples and in the claims.

Some preferred aspects include:

A method or a saccharide or a product or a use or an amino acid sequence or a nucleotide sequence according to the present invention wherein the alcohol dehydrogenase is selected from alcohol dehydrogenases in enzyme class EC 1.1.5.

A method or a saccharide or a product or a use or an amino acid sequence or a nucleotide sequence according to the present invention wherein the alcohol dehydrogenase is selected from alcohol dehydrogenases in enzyme class EC 1.1.5.2.

A method or a saccharide or a product or a use or an amino acid sequence or a nucleotide sequence according to the present invention wherein the alcohol dehydrogenase is selected from alcohol dehydrogenases in enzyme class EC 1.1.1.

A method or a saccharide or a product or a use or an amino acid sequence or a nucleotide sequence according to the present invention wherein the alcohol dehydrogenase is selected from alcohol dehydrogenases in enzyme classes EC 1.1.1.1 and EC 1.1.1.2.

A method or a saccharide or a product or a use or an amino acid sequence or a nucleotide sequence according to the present invention wherein the NAD+ or NADP+ cofactor is present in a concentration of 0.01-5000 ppm by weight.

A method or a saccharide or a product or a use or an amino acid sequence or a nucleotide sequence according to the present invention wherein the NAD+ or NADP+ is present in a concentration of 0.10-1000 ppm by weight.

DETAILED DESCRIPTION OF PREFERRED EMBODIMENTS

Figure 1:
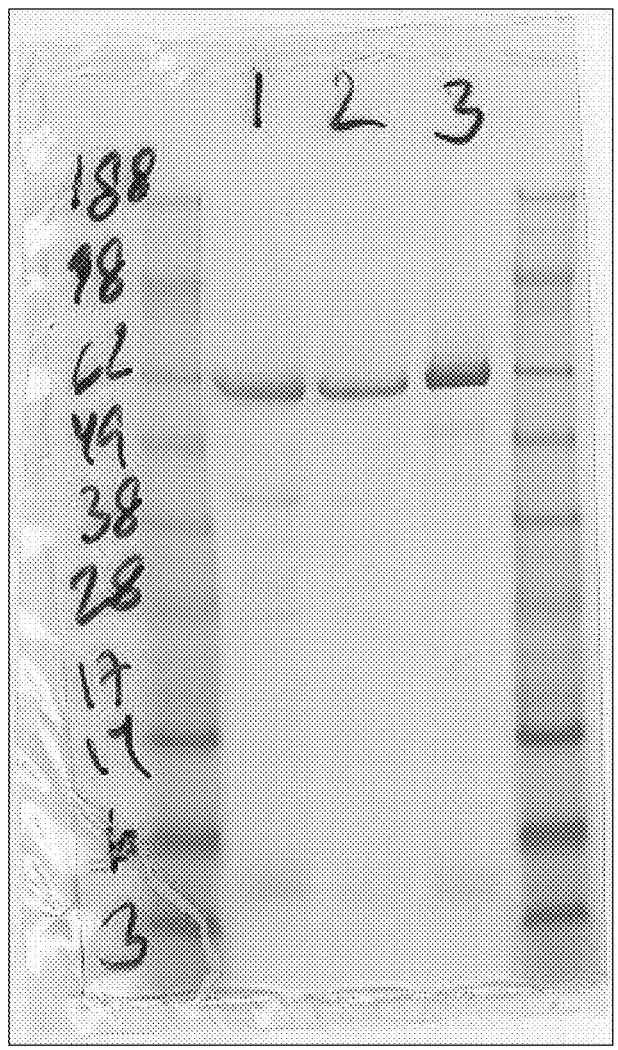
FIG. 1 illustrates an SDS-PAGE of extracellular broth from fermentation of a Pichia pastoris recombinant strain harbouring the PQQ-ADH gene.

The present invention comprises in one aspect a method of oxidising a polysaccharide by contacting the polysaccharide with an alcohol dehydrogenase (ADH) enzyme selected from a quinone redox cofactor-dependent ADH, a nicotinamide adenine dinucleotide ($NAD^+$) redox cofactor-dependent ADH, a nicotinamide adenine dinucleotide phosphate ($NADP^+$) redox cofactor-dependent ADH, and any combination thereof.

Saccharides

In this specification the term 'saccharide' is intended to cover all saccharides (sugars), including naturally occurring and synthetic and semi-synthetic saccharides. The term encompasses monosaccharides (i.e. saccharides that cannot be hydrolyzed into simpler sugars), disaccharides (i.e. compounds having two monosaccharide units (moieties) joined together by a glycoside bond), oligosaccharides (i.e. compounds having 3 to 10 monosaccharide units joined together by glycoside bonds in a branched or unbranched chain or a ring (optionally having a saccharide side chain). and polysaccharides. i.e. compounds having over 10 monosaccharide units joined together by a glycoside bond in a branched or unbranched chain or a ring (optionally having a saccharide side chain).

The saccharide may be bonded to other molecules, such as biomolecules, for example peptides, polypeptides/proteins (inc. enzymes), lipids and nucleic acids. However, it is preferred for the purposes of the present invention that the saccharide is formed from monosaccharide units only.

In one embodiment, the saccharide is a monosaccharide, i.e. a saccharide that cannot be hydrolyzed into a simpler sugar. The monosaccharide may have the D- or L-configuration, and may be an aldose or ketose.

In one embodiment, the monosaccharide is a hexose, examples of which include aldohexoses such as glucose, galactose, allose, altrose, mannose, gulose, idose and talose and ketohexoses such as fructose, tagatose, psicose and sorbose. Preferably, the hexose is glucose or galactose.

In another embodiment, the monosaccharide is a pentose, examples of which include aldopentoses such as ribose, arabinose, xylose and lyxose and ketopentoses such as ribulose and xylulose. Preferably, the pentose is arabinose or xylose.

In an alternative embodiment, the saccharide is a higher saccharide, i.e. a saccharide comprising more than one monosaccharide moiety joined together by glycoside bonds and which are generally hydrolysable into their constituent monosaccharides. Examples of such higher saccharides include disaccharides (2 monosaccharide moieties), oligosaccharides (3 to 10 monosaccharide moieties) and polysaccharides (more than 10 monosaccharide moieties). In this regard, the monosaccharide moieties which form the higher saccharide may be the same or different, and may each independently have the D- or L-configuration, and may each independently be aldose or ketose moieties.

The monosaccharide units which form the higher saccharide may have the same or different numbers of carbon atoms. In one embodiment, the monosaccharide moieties of the higher saccharide are hexose moieties, examples of which include aldohexoses such as glucose, galactose, allose, altrose, mannose, gulose, idose and talose and ketohexoses such as fructose, tagatose, psicose and sorbose. Preferably, the hexose moieties of such a higher saccharide are glucose moieties.

In another embodiment, the monosaccharide moieties of the higher saccharide are aldopentose moieties such as ribose, arabinose, xylose and lyxose and ketopentoses such as ribulose and xylulose. Preferably, the pentose moieties of such a higher saccharide are arabinose or xylose moieties.

The monosaccharide moieties which form the higher saccharide are joined together by glycoside bonds. When the monosaccharide moieties are hexose moieties, the glycoside bonds may be 1,4'-glycoside bonds (which may be 1,4'-α- or 1,4'-β-glycoside bonds), 1,6'-glycoside bonds (which may be 1,6'-α- or 1,6'-β-glycoside bonds), 1,2'-glycoside bonds (which may be 1,2'-α- or 1,2'-β-glycoside bonds), or 1,3'-glycoside bonds (which may be 1,3'-α- or 1,3'-β-glycoside bonds), or any combination thereof.

In one embodiment, the higher saccharide comprises 2 monosaccharide units (i.e. is a disaccharide). Examples of suitable disaccharides include lactose, maltose, cellobiose, sucrose, trehalose, isomaltulose and trehalulose.

In another embodiment, the higher saccharide comprises 3 to 10 monosaccharide units (i.e. is an oligosaccharide). The monosaccharide units may be in a chain, which may be branched or unbranched: such oligosaccharides are referred to in this specification as 'chain oligosaccharides'. Examples of such oligosaccharides include maltotriose, maltotetraose, maltopentaose, maltohexaose, maltoheptaose, cellobiose, cellotriose, cellotetraose, cellopentaose, cellohexaose and celloheptaose, as well as fructo-oligosaccharides (FOS) which consist of short chains of fructose molecules; mannanoligosaccharides, isomaltooligosaccharides, galactooligosaccharides and xylooligosaccharides.

Alternatively, the monosaccharide units which form the oligosaccharide may form a ring, which may optionally have a saccharide side chain: such oligosaccharides are referred to in this specification as 'cyclic oligosaccharides'. Typically, the ring consists of 5 to 8 monosaccharide units, preferably 6 to 8, and more preferably 6 monosaccharide units: the side chain, where present, typically consists of 1 to 4 monosaccharide units, preferably 1 or 2.

In particular, the cyclic oligosaccharide may be a cyclodextrin. Cyclodextrins (sometimes called cycloamyloses) make up a family of cyclic oligosaccharides, composed of 5 or more α-D-glucopyranoside units linked 1→4, as in amylose (a fragment of starch). The 5-membered macrocycle is not natural. Typical cyclodextrins contain a number of glucose monomers ranging from six to eight units in a ring, creating a cone shape. Particularly preferred cyclodextrins are α-cyclodextrin (6-membered sugar ring molecule), β-cyclodextrin: (7-membered sugar ring molecule) and γ-cyclodextrin (8-membered sugar ring molecule).

In another embodiment, the higher saccharide is a polysaccharide, comprising at least 10 monosaccharide units joined together by glycoside bonds. Typically such polysaccharides, comprise at least about 40, for example at least about 100, such as at least about 200, including at least about 500, for example at least about 1000, such as at least about 5000, for example about 10000, such as at least about 50000, for example about 100000, monosaccharide units.

The monosaccharide units in such a polysaccharide may be joined in a chain, which may be branched or unbranched: such polysaccharides are referred to in this specification as 'chain polysaccharides'. Alternatively, the monosaccharide units may be joined in a ring (which may have for example about 10 to about 200, preferably about 10 to about 100, more preferably about 10 to about 50, and most preferably about 10 to about 20, monosaccharide units), which may have one or more (preferably 1 or 2) side chains each comprising 1 to 6 (preferably 1 to 4, more preferably 1 or 2) monosaccharide units: such polysaccharides are referred to in this specification as 'cyclic polysaccharides'.

In some embodiments, the polysaccharide comprises from 10 to 500000 monosaccharide units. In other embodiments, the polysaccharide comprises from about 100 to about 1000 monosaccharide units. In other embodiments, the polysaccharide comprises from about 1000 to about 10000 monosaccharide units. In other embodiments, the polysaccharide comprises from about 10000 to about 100000 monosaccharide units. In some embodiments, the polysaccharide comprises from 40 to 3000, preferably about 200 to about 2500, monosaccharide units.

Examples of such polysaccharides include starch and derivatives thereof (such as cationic or anionic, oxidised or phosphated starch), amylose, amylopectin, glycogen, cellulose or a derivative thereof (such as carboxymethyl cellulose), alginic acid or a salt or derivative thereof, polydextrose, pectin, pullulan, carrageenan, locust bean gum and guar and derivatives thereof (such as cationic or anionic guar).

In one embodiment, the polysaccharide comprises starch or a derivative thereof. Starches are glucose polymers in which glucopyranose units are bonded by α-linkages. It is made up of a mixture of amylose and amylopectin. Amylose consists of a linear chain of several hundred glucose molecules linked together by 1,4'-α-glycoside linkages. In contrast amylopectin is a branched molecule made of several thousand glucose units, the main chain comprising 1,4'-α-glycoside linkages but having 1,6'-α-glycoside branches approximately every 25 glucose units.

Derivatives of starch are also oxidisable according to the present invention, provided that the derivative contains sufficient free primary hydroxyl groups for the enzyme to act upon (i.e. the starch has a degree of substitution of less than 1). Examples of suitable starches include substituted starches (eg carboxymethyl starch) and cationic, anionic, oxidised and phosphated starches.

In one embodiment, the polysaccharide comprises glycogen. Glycogen is a polysaccharide that is found in animals and is composed of a branched chain of glucose residues.

In one embodiment, the polysaccharide comprises cellulose or a derivative thereof. Cellulose is a polymer formed from several thousand glucose units bonded together by 1,4'-β-glycoside linkages. Derivatives of cellulose are known in the art, and include hydroxyalkylcelluloses such as hydroxymethylcellulose, hydroxyethyl-cellulose, hydroxypropylcellulose and hydroxypropylmethylcellulose and carboxyalkylcelluloses such as carboxymethylcellulose and carboxyethylcellulose. Derivatives of cellulose are also oxidisable according to the present invention, provided that the derivative contains sufficient free primary hydroxyl groups for the enzyme to act upon (i.e. the cellulose has a degree of substitution of less than 1).

Oxidation

The method of the invention comprises oxidising a saccharide, as defined and exemplified above, with an alcohol dehydrogenase (ADH) enzyme, as defined and exemplified herein.

The method of the invention results in oxidation of a proportion of the primary alcohol groups of the monosaccharide, or of the monosaccharide moieties of the higher saccharide, to aldehyde groups. The extent of oxidation, and the consequent degree of substitution (D.S.) of the resulting polymer (where the substrate is a higher saccharide), depends on factors such as the substrate, type and concentration of ADH enzyme employed, the type and concentration of cofactor (where used), and the reaction conditions such as temperature and pressure.

Typically, the method of the invention results in oxidation of at least 2%, such as at least 3%, for example at least 4%, such as at least 5%, for example at least 6%, of the primary alcohol groups of the monosaccharide, or of the monosaccharide moieties of the higher saccharide, to aldehyde groups. In particular, where the substrate is a higher saccharide (in particular, a polysaccharide) composed of glucose moieties, at least 2%, such as at least 3%, for example at least 4%, such as at least 5%, for example at least 6%, of the primary alcohol groups at the C-6 position of the glucose units of the higher saccharide, may be oxidised to aldehyde groups.

Therefore, the invention preferably comprises a method of oxidising a higher saccharide (in particular, a polysaccharide) formed from glucose moieties, wherein at least 2%, such as at least 3%, for example at least 4%, such as at least 5%, for example at least 6%, of the primary alcohol groups at the C-6 position of the glucose units of the polysaccharide, are oxidised to aldehyde groups, by contacting the polysaccharide with an alcohol dehydrogenase (ADH) enzyme, as defined and exemplified herein.

The oxidation method of the present invention may result in some of the primary alcohol groups of the monosaccharide, or of the monosaccharide moieties of the higher saccharide, being oxidised to a carboxylic acid. The extent of oxidation of —$CH_2OH$ to —$CO_2H$ groups, and the consequent degree of substitution (D.S.) of the resulting polymer (where the substrate is a higher saccharide), depends on factors such as the substrate, the type and concentration of ADH enzyme employed, the type and concentration of cofactor (where used), and the reaction conditions such as temperature and pressure. Typically, the method of the invention results in oxidation of at least 0.05%, such as 0.05-0.5%, of the primary alcohol groups of the monosaccharide, or of the monosaccharide moieties of the higher saccharide, to carboxylic acid groups.

Alcohol Dehydrogenase

The method of the present invention employs, as an active ingredient, an alcohol dehydrogenase (ADH) enzyme. Alcohol dehydrogenase (ADH) is an oxidoreductase enzyme first discovered in the mid-1960s in *Drosophila melanogaster*. Alcohol dehydrogenases are a group of seven dehydrogenase enzymes that occur in many organisms and facilitate the interconversion between alcohols and aldehydes or ketones. In humans and many other animals, they serve to break down alcohols which could otherwise be toxic; in yeast and many bacteria, some alcohol dehydrogenases catalyze the opposite reaction as part of fermentation.

In this specification the term 'alcohol dehydrogenase', when used in isolation, covers all enzymes capable of acting on a >CH—OH group to oxidise it to a >C=O group (or the reverse reaction), in the presence or absence of a cofactor. Such enzymes are also known as 'aldehyde reductase' when the reverse reaction (i.e. reduction of a >C=O group to a >CH—OH group) occurs.

The activity of some ADH enzymes is dependent on the presence of a redox cofactor. Such ADH enzymes are referred to in this specification as 'redox cofactor-dependent alcohol dehydrogenases' and are used in this invention.

In particular, the ADH used in the present invention is selected from a quinone redox cofactor-dependent ADH, a nicotinamide adenine dinucleotide ($NAD^+$) redox cofactor-dependent ADH, a nicotinamide adenine dinucleotide phosphate ($NADP^+$) redox cofactor-dependent ADH, and any combination thereof. The function of the redox cofactors is described in more detail below.

The present invention is based on the surprising finding that quinone-dependent ADH and $NAD^+/NADP^+$ dependent alcohol dehydrogenases are capable of selectively oxidising the primary alcohol groups of a monosaccharide, or of the monosaccharide moieties of a higher saccharide (in particular, of a polysaccharide) to aldehyde groups. This is contrary to what would have been expected as it would not previously have been thought that this type of alcohol dehydrogenase would be effective on this type of substrate. This has the potential to enable modification of the physico-chemical properties of saccharides, especially polysaccharides, by enzymatic techniques and avoid the use of harsh reagents.

In particular, the present invention is based on the surprising finding that quinone-dependent ADH and $NAD^+/NADP^+$ dependent alcohol dehydrogenases are capable of selectively oxidising the C-6 or C-5 position of hexose or pentose rings, respectively.

Some alcohol dehydrogenases, especially ADHs falling within enzyme class (E.C.) 1.1.1, particularly E.C. 1.1.1.1 or E.C. 1.1.1.2, as well as those falling within enzyme class (E.C.) 1.2.1, generally function in conjunction with the redox cofactor nicotinamide adenine dinucleotide ($NAD^+$) or nicotinamide adenine dinucleotide phosphate ($NADP^+$), the reaction proceeding with the reduction of $NAD^+$ or $NADP^+$ to NADH or NADPH respectively.

Other alcohol dehydrogenases, especially those falling within enzyme class EC 1.1.5, particularly EC 1.1.5.2, generally function in conjunction with a quinone redox cofactor, particularly a quinone cofactor selected from pyrroloquinoline quinone (PQQ), tryptophyl tryptophanquinone (TTQ), topaquinone (TPQ), and lysine tyrosylquinone (LTQ), the quinone group being reduced to a di- or tetrahydroquinone group during the reaction.

In one embodiment, the ADH is selected from enzyme class (E.C.) 1.1.1 or 1.1.5. Of the ADH enzymes in E.C. 1.1.1, preferred are those in classification 1.1.1.1 or 1.1.1.2. Of the ADH enzymes in E.C. 1.1.5, preferred are those in classification 1.1.5.2.

In another embodiment, the ADH is selected from the aldehyde reductases of enzyme class (E.C.) 1.2.1. These enzymes catalyse the opposite reaction of the ADHs and it is known that many enzymes can work as catalyst for both the forward and the reverse reaction depending on conditions.

In one embodiment, the ADH is obtainable or is obtained from a living organism. Suitable ADH's are of bacterial or fungal origin. Preferred are ADH enzymes of bacterial origin, especially *Pseudogluconobacter saccharoketogenes* ADH, *Lactobacillus kefir* ADH, *Thermoanaerobium brockii* ADH and *Escherichia coli* ASD, or an alcohol dehydrogenase enzyme having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity to any thereof. Particularly preferred is *Pseudogluconobacter saccharoketogenes* ADH or an alcohol dehydrogenase enzyme having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity thereto. Among ADH enzymes of fungal origin, *Saccharomyces cerevisiae* ADH, or an alcohol dehydrogenase enzyme having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity thereto, is preferred.

Amino Acid Sequences

Amino acid sequences of ADH enzymes having the specific properties as defined herein, particularly those of SEQ ID Nos. 1, 1A, 2, 2a, 3, 4, 5 or 5a, defined below, may be used in the present invention.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein used in the present invention may be used in conjunction with other proteins, particularly other enzymes, for example amylases, proteases or lipases. Thus the present invention also covers a composition comprising a combination of enzymes wherein the combination comprises the ADH enzyme used in the present invention and another enzyme, which may be, for example, another ADH enzyme as described herein, or a protease. This aspect is discussed in a later section.

Sequence Identity/Sequence Homology/Variants/Homologues/Derivatives

The present invention also encompasses the use of polypeptides having a degree of sequence identity (sometimes referred to as sequence homology) with amino acid sequence(s) defined herein or with a polypeptide having the specific properties defined herein. The present invention encompasses, in particular, polypeptides having a degree of sequence identity with any of SEQ ID Nos. 1, 1A, 2, 2a, 3, 4, 5 or 5a, defined herein, or homologues thereof. Here, the term "homologue" means an entity having sequence identity with the subject amino acid sequences or the subject nucleotide sequences. Here, the term "homology" can be equated with "sequence identity".

In a preferred embodiment, the enzyme has the amino acid sequence shown in SEQ ID No 1 or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

In a preferred embodiment, the enzyme has the amino acid sequence shown in SEQ ID No 1A or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

In a preferred embodiment, the enzyme has the amino acid sequence shown in SEQ ID No 2 or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

The enzyme may have the amino acid sequence shown in SEQ ID No. 2A or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

In a preferred embodiment, the enzyme has the amino acid sequence shown in SEQ ID No 3 or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

In a preferred embodiment, the enzyme has the amino acid sequence shown in SEQ ID No 4 or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

In a preferred embodiment, the enzyme has the amino acid sequence shown in SEQ ID No 5 or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

The enzyme may have the amino acid sequence shown in SEQ ID No. 5A or an amino acid sequence having at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, amino acid sequence identity therewith.

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 50%, preferably at least 55%, such as at least 60%, for example at least 65%, at least 70%, at least 75%, at least 80%, at least 85%, at least 90%, at least 95%, at least 96%, at least 97%, at least 98% or at least 99%, identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

(i) assignment of a penalty score each time a gap is inserted (gap penalty score),
(ii) assignment of a penalty score each time an existing gap is extended with an extra position (extension penalty score),
(iii) assignment of high scores upon alignment of identical amino acids, and
(iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools are available from the ExPASy Proteomics website. Another example of software that can perform sequence alignment is BLAST (Basic Local Alignment Search Tool), which is available from the webpage of National Center for Biotechnology Information and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage under tools—sequence analysis—ClustalW2.

Thus, the present invention also encompasses the use of variants, homologues and derivatives of any amino acid sequence of a protein as defined herein, particularly those of SEQ ID Nos. 1, 1A, 2, 2a, 3, 4, 5 or 5a, defined herein.

The sequences, particularly those of SEQ ID Nos. 1, 1A, 2, 2a, 3, 4, 5 or 5a, may also have deletions, insertions or substitutions of amino acid residues which produce a silent change and result in a functionally equivalent substance.

Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell D C. (1995).

The ADH may be selected from *Pseudogluconobacter saccharoketogenes* ADH (SEQ ID No 1), *Pseudogluconobacter saccharoketogenes* ADH (SEQ ID No 1A), *Lactobacillus kefir* ADH (SEQ ID No 2), *Lactobacillus kefir* ADH (SEQ ID No 2a), *Saccharomyces cerevisiae* ADH (SEQ ID No 3) or *Thermoanaerobium brockii* ADH (SEQ ID No 4), *Escherichia coli* ASD (SEQ ID No 5) or *Escherichia coli* ASD (SEQ ID No 5a).

In preferred embodiments, the ADH is selected from *Pseudogluconobacter saccharoketogenes* ADH (SEQ ID No 1), *Pseudogluconobacter saccharoketogenes* ADH (SEQ ID No 1A), *Lactobacillus kefir* ADH (SEQ ID No 2), *Saccharomyces cerevisiae* ADH (SEQ ID No 3) or *Thermoanaerobium brockii* ADH (SEQ ID No 4), or *Escherichia coli* ASD (SEQ ID No 5).

In one preferred embodiments the ADH is selected from *Pseudogluconobacter saccharoketogenes* ADH (SEQ ID No 1) and *Pseudogluconobacter saccharoketogenes* ADH (SEQ ID No 1A).

In one aspect, preferably the ADH enzyme used in the present invention is in a purified form. The term "purified" means that a given component is present at a high level. The component is desirably the predominant active component present in a composition.

Isolated and/or Purified

In one aspect, preferably the ADH enzyme used in the present invention is in an isolated form. The term "isolated" means that the product is at least substantially free from at least one other component with which the product is associated in the reaction mixture.

In one aspect, preferably the product according to the present invention is in a purified form. The term "purified" means that a given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

Concentration

The ADH enzyme may be present in any concentration to enable it to perform the required function of oxidising the polysaccharide. The concentration of ADH required depends on factors such as the method of purification and the concentration of any cofactor (where present). Suitably, the ADH is present in a concentration of at least about 0.05 ppm (by weight), such as, e.g. at least about 1 ppm, at least about 10 ppm, at least about 100 ppm, at least about 150 ppm or at least about 200 ppm. Preferably, the ADH is present in a concentration of about 0.05-500 ppm, preferably about 0.1-200 ppm, more preferably about 0.2-100 ppm, even more preferably about 0.5-50 ppm, yet more preferably about 1-50 ppm, and most preferably about 1-10 ppm (by weight).

Redox Cofactors

As noted above, ADH is preferably used in the present invention with a redox cofactor. In this specification the term 'redox cofactor' is defined as any non-protein chemical compound that assists the enzymatic redox reaction. The cofactor may be tightly bound or loosely bound to the enzyme, or unbound.

Cofactors can be divided into two broad groups: coenzymes and prosthetic groups. Coenzymes are small organic non-protein molecules that carry chemical groups between enzymes. These molecules are not bound tightly by enzymes and are released as a normal part of the catalytic cycle. In contrast, prosthetic groups form a permanent part of the protein structure.

In one embodiment, the cofactor is nicotinamide adenine dinucleotide (NAD⁺) or nicotinamide adenine dinucleotide phosphate (NADP⁺). When these compounds are used as the cofactor, the reaction typically proceeds with the reduction of NAD⁺ or NADP⁺ to NADH or NADPH respectively. In this specification the terms NAD⁺ and NADP⁺ encompasses the redox cofactors nicotinamide adenine dinucleotide (NAD⁺) or nicotinamide adenine dinucleotide phosphate whether in their oxidised (positively charged) form or their reduced form (usually described as NADH and NADPH).

NAD⁺ or NADP⁺ cofactors are particularly preferred when the ADH is an ADH enzyme in subclass 1.1.1, particularly ADH enzymes in E.C. 1.1.1.1 or 1.1.1.2, or is an ADH enzyme in subclass 1.2.1. NAD⁺ or NADP⁺ cofactors are especially preferred when the ADH is *Lactobacillus kefir* ADH (SEQ ID No 2), *Saccharomyces cerevisiae* ADH (SEQ ID No 3) or *Thermoanaerobium brockii* ADH (SEQ ID No 4).

The enzyme cofactors may be present in any concentration to enable the enzyme to perform the required function of oxidising a saccharide. Suitably, the NAD⁺ or NADP⁺ cofactor is present in a concentration of about 0.01 to about 5000 ppm by weight. More preferably, the NAD⁺ or NADP⁺ is present in a concentration of about 0.10 to about 1000 ppm by weight.

In another embodiment, the cofactor is a quinone cofactor. In this specification the term 'quinone cofactor' covers any compound including a 6-membered (saturated or partially unsaturated) ring having two carbonyl (>C=O) groups as ring substituents, and which is capable of acting as a cofactor for ADH. 1,4-quinones and 1,2-quinones, for example those of the general formulae below (wherein the wavy bonds represent attachments to the remainder of the molecule, including molecules wherein two bonds together with the carbon atoms to which they are attached form a ring) are preferred. Quinone cofactors are particularly preferred when the ADH is an ADH enzyme in subclass 1.1.5, particularly ADH enzymes in E.C. 1.1.5.2, and especially when the ADH enzyme is *Pseudogluconobacter saccharoketogenes* ADH (SEQ ID No 1) or *Escherichia coli* ADH (SEQ ID No 5).

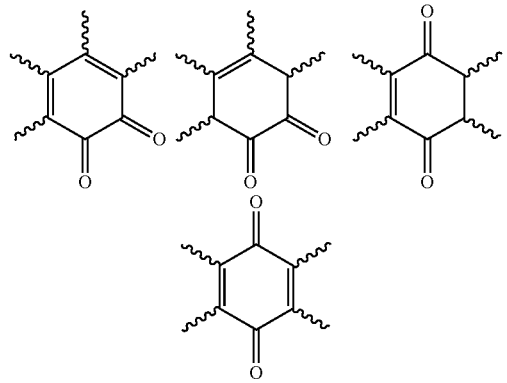

Preferably, the quinone cofactor is selected from from pyrroloquinoline quinone (PQQ), tryptophyl tryptophanquinone (TTQ), topaquinone (TPQ), and lysine tyrosylquinone (LTQ), the structures of which are set out below, or acceptable salts, esters or other derivatives thereof.

Acceptable salts of the quinone cofactors used in the present invention include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Acceptable esters of the quinone cofactors used in the present invention, in particular PQQ, include ($C_{1-6}$)alkyl esters, halo($C_{1-6}$)alkyl esters, hydroxy($C_{1-6}$)alkyl esters and ($C_{1-6}$)alkoxy($C_{1-6}$)alkyl esters, and benzyl esters. Other acceptable derivatives include N-oxide derivatives.

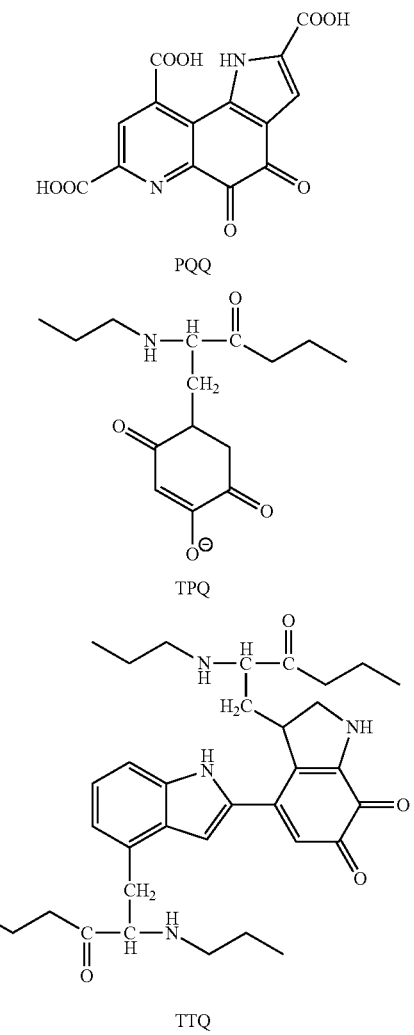

-continued

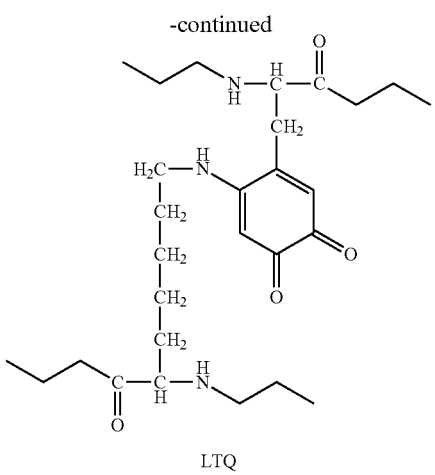

LTQ

More preferably, the quinone cofactor is pyrroloquinoline quinone (PQQ) or an acceptable salt, ester or other derivative thereof. Alcohol dehydrogenase enzymes used with PQQ as cofactor are referred to in this specification as "PQQ-ADH enzymes".

When the quinone cofactor is pyrroloquinoline quinone (PQQ), the PQQ may be made synthetically, for example as described in Buchi, G., J. H. Botkin, G. C. M. Lee, and K. Yakushijin, *J. Am. Chem. Soc.* (1985) 107, 5555-5556. Alternatively, the PQQ may be obtained from natural sources, particularly foods, as described for example in Kumazawa et al., *Biochem. J.* (1995) 307, 331-333. Examples of foodstuffs containing PQQ include broad bean, green soybeans, potato, sweet potato, parsley, cabbage, carrot, celery, green pepper, spinach, tomato, apple, banana, kiwi fruit, orange, papaya, green tea, oolong (tea), cola, whiskey, wine, sake, bread, fermented soybeans (natto), miso (bean paste) and tofu (bean curd). Preferred sources of PQQ are plant extracts. A particularly preferred source of PQQ is green tea extract, as this is cheap and widely available.

When the quinone cofactor is PQQ, the PQQ is preferably present in a concentration of about 0.01 to about 1000 ppm, such as e.g., about 0.1 to about 500 ppm, about 0.15 to about 250 ppm or about 0.2 to about 100 ppm. More preferably, the PQQ is present in a concentration of about 0.25 to about 10 ppm.

When a quinone is used as cofactor with the ADH enzyme, a metal ion is preferably also used in conjunction with the ADH and quinone. Without wishing to be bound by theory, it is believed that the metal ion coordinates to the quinone and the substrate, thereby assisting transfer of hydrogen from the substrate to the quinone. Examples of suitable metal ions include alkali metal ions such as lithium, sodium and potassium ions, alkaline earth metal ions such as magnesium and calcium ions, and transition metal ions such as iron, manganese, cobalt, copper, molybdenum and zinc ions, or any combination thereof. Divalent or trivalent metal ions are preferred and calcium ions or iron ($Fe^{2+}/Fe^{3+}$) ions, or any combination thereof are particularly preferred.

According to Toyama et al, *Arch. Biochem. Biophys.* (2004) 428, 10-21, quino(hemo)protein alcohol dehydrogenases (ADH) that have pyrroloquinoline quinone (PQQ) as the cofactor group are classified into 3 groups, types I, II, and III. Type I ADH is a simple quinoprotein having PQQ as the only cofactor group, while type II and type III ADHs are quinohemoprotein having heme c as well as PQQ in the catalytic polypeptide. Type II ADH is a soluble periplasmic enzyme and is widely distributed in *Proteobacteria* such as *Pseudomonas, Ralstonia, Comamonas*, etc. In contrast, type III ADH is a membrane-bound enzyme working on the periplasmic surface solely in acetic acid bacteria. It consists of three subunits that comprise a quinohemoprotein catalytic subunit, a triheme cytochrome c subunit, and a third subunit of unknown function. The present invention embraces compositions and methods using all three types of ADH as defined in the above article; Type I ADH is preferred.

Combinations

The ADH enzyme may be used according to the present invention in combination with one or more further active agents. Such combinations may offer advantages, including synergy, when used together in the oxidation method of the invention.

In particular, the ADH enzyme may be used according to the present invention in combination with one or more further enzymes as active agents. Such combinations may offer advantages, including synergy, when used together in the oxidation method of the invention.

In one embodiment, the further enzyme is another ADH enzyme, so that two (or more) different ADH enzymes are used in combination.

In another embodiment, the ADH may be used in combination with a further active agent, capable of converting the aldehyde groups of the monosaccharide, or of the monosaccharide moieties of the higher saccharide, to carboxylic acid groups. Such a combination offers advantages in that the oxidized saccharide/polysaccharide would be rendered more suitable for ingestion for food applications. Examples of such a further active agent capable of the above conversion to carboxylic acid include aldehyde dehydrogenase or oxidase (can be found in EC 1.2.).

Thus, in a preferred aspect, the method of the present invention comprises contacting the saccharide with an alcohol dehydrogenase (ADH) enzyme selected from a quinone redox cofactor-dependent ADH and a nicotinamide adenine dinucleotide ($NAD^+$) or nicotinamide adenine dinucleotide phosphate ($NADP^+$) redox cofactor-dependent ADH, and an aldehyde dehydrogenase or oxidase.

Applications

The method of the present invention has a wide range of applications. In particular, the method of the present invention is useful in the food and paper industries.

In one aspect, the method of the present invention can be used to prepare modified polysaccharides useful in the paper industry. Examples of polysaccharides that are typically relevant for the paper industry include cationic, anionic, oxidized and phosphated starches; carboxymethyl cellulose (CMC), guar, alginate, guar, cationic guar and anionic guar. Further details of suitable polysaccharides may be found in US2003/150573.

Thus, in one aspect, the invention comprises a paper product including an oxidised saccharide (in particular, an oxidised polysaccharide, as defined and exemplified above) prepared by the method of the invention, as defined above, either in its broadest aspect or a preferred aspect, as well as a method of producing a paper product including such an oxidised saccharide (in particular, an oxidised polysaccharide).

A typical paper production method may include the following steps:
 (a) Chemical or mechanical pulping to produce wood pulp which helps to release cellulose
 (b) Refining to process and soften the fibres
 (c) Dewatering on a mesh and forming of sheets
 (d) Pressing
 (e) Drying
 (f) Calendaring to smooth the surface
 (g) Coating The above steps may be varied within the ambit of knowledge of a person skilled in the art.

For application in the food industry, at least a portion of the saccharide may be comprised in a flour. The flour may be mixed with conventional ingredients to prepare a dough. Examples of such ingredients include yeast, water, egg, milk, salt, sugar, fat and oil. The dough may then be baked to prepare a baked product.

As an alternative application in the food industry, at least a portion of the saccharide is comprised in a sugar product, for example sucrose, invert sugar, glucose, fructose or maltose.

The invention will now be described, by way of example only, with reference to the following Figures and non-limiting Examples.

EXAMPLES

The PQQ-ADH enzyme used in the examples is SEQ ID NO. 1a, which is the enzyme prepared in "preparation 1".

Preparation 1: *Pseudogluconobacter saccharoketogenes* ADH

Figure 4:
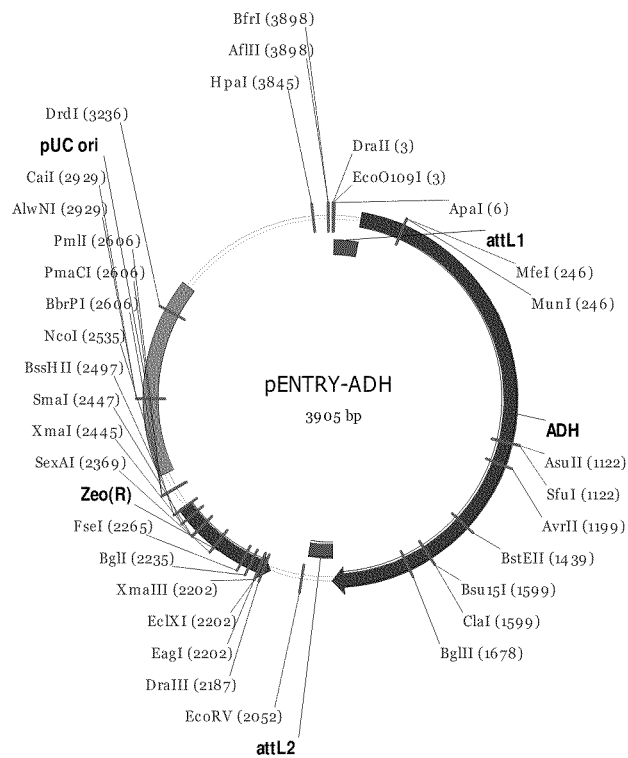
FIG. 4 is a plasmid map of pENTRY-ADH containing the PQQ dependent ADH gene, Gateway compatible attLsites and the Zeocin selection marker.

The gene encoding the *Pseudogluconobacter saccharoketogenes* PQQ-dependent alcohol dehydrogenase gene (PQQ-ADH) was synthesized as a codon optimized fragment, including its own signal sequence, and cloned into the pDONR/Zeo via the Gateway® BP recombination reaction (Invitrogen, Carlsbad, Calif., USA) resulting in the entry vector pENTRY-ADH (FIG. 4). SEQ ID No. 6 shows the DNA sequence of the codon optimized PQQ-ADH gene (from Geneart AG (Regensburg, Germany)). Shown in italics are the sequences flanking the PQQ-ADH ORF. These flanking sequences contain the attB sites that facilitate the Gateway® BP dependent cloning of the gene into pDONR/Zeo.

To enable the expression of the PQQ-ADH in *Pichia pastoris*, the gene was cloned from pENTRY-ADH into pPIC2-DEST (FIG. 5) via the Gateway® LR recombination reaction. The resulting plasmid, pPIC2-ADH (FIG. 6) was linearized by SalI digestion, enabling integration of the construct into the HIS4 locus of *P. pastoris* GS115 upon transformation. This vector contains the *P. pastoris* strong AOX1 promoter, allowing for strong methanol-inducible gene expression. For production of PQQ-ADH, *P. pastoris*::pPIC2-ADH was grown in a 2 liter B. Braun Biostat B fermentor according to standard *P. pastoris* fermentation protocols (Invitrogen, Carlsbad, Calif. USA). During fermentation the major fraction of the expressed PQQ-ADH was found in the culture supernatant, with levels reaching 100-400 mg/l 72 hours after the start of methanol induction. The N-terminus of the mature protein was found to start at position 37 of the coding part, thus starting with AEPSKAGQSA.

The N-terminus of the PsADH expressed by *Pichia pastoris* was determined by Edman degradation and analysis on a Procise® cLC capillary 491 protein sequencing system (Applied Biosystems).

Figure 5:
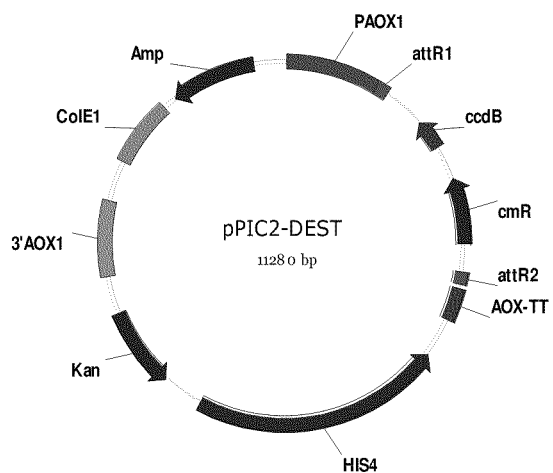
FIG. 5 is a plasmid map of the *P. pastoris* destination vector pPIC2-DEST, which was derived from pPIC3.5K (Invitrogen).
Figure 6:
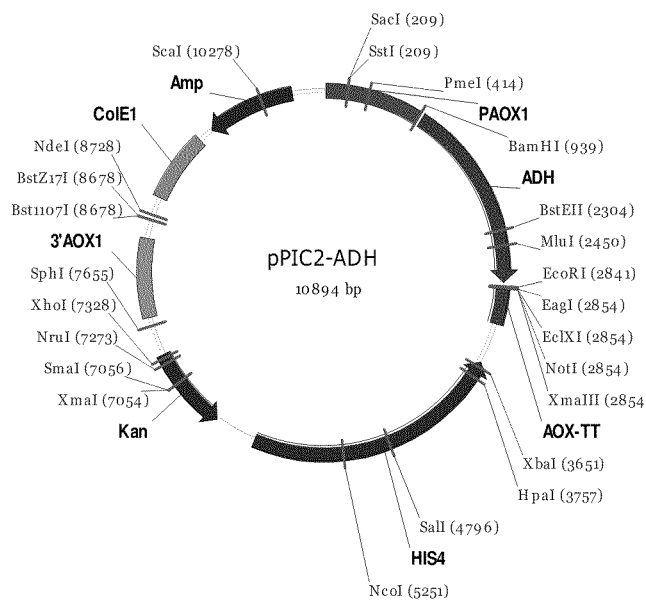
FIG. 6 is a plasmid map of the *P. pastoris* PQQ-ADH expression plasmid pPIC2-ADH.
Figure 7:
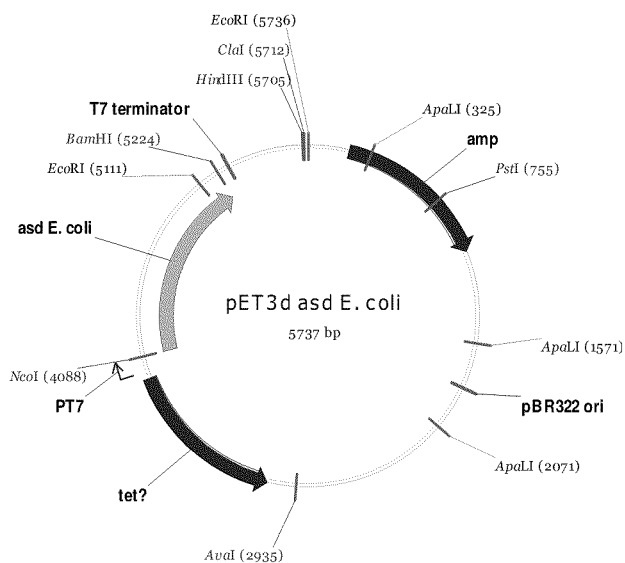
FIG. 7 is a map of the plasmid pET3d-asd expressing the *E. coli* aldose sugar dehydrogenase ylil.

FIG. 5 is a plasmid map of the *P. pastoris* destination vector pPIC2-DEST, which was derived from pPIC3.5K (Invitrogen). The vector contains the methanol inducible Gateway® cassette was inserted between promoter and terminator of pPIC3.5K, and consists of the recombination sites attR1 and 2, the chloramphenicol resistance marker (cmR) and ccdB gene for negative selection in the Gateway® cloning procedure. Furthermore, the vector contains the HIS4 gene for selection in *P. pastoris*, the kanamycin (Kan) and ampicilin (Amp) resistance genes for selection in *E. coli* (Kan).

Example 1

Expression of the PQQ-ADH Gene

A synthetic PQQ-ADH gene with a broad host codon usage was ordered and cloned into Gateway compatible expression vectors. Acceptable expression levels (0.4 g/l) were obtained after fermentation of a *Pichia pastoris* recombinant strain. A SDS-gel analysis of extracellular broth showed a dominant band of the right size (FIG. 1).

FIG. 1 is a SDS-PAGE of extracellular broth from fermentation of a *Pichia pastoris* recombinant strain harboring the PQQ-ADH gene. The molecular weight markers are as follows:

Lane 1: Fermentation broth, approximately 3 µg protein)
Lane 2: Fermentation broth (approximately 2 µg protein)
Lane 3: Fermentation broth (approximately 6 µg protein)
Nu-PAGE, 4-12%, Mes, +DTT
Expression could be estimated at the levels of 0.4 g/l.

Example 2

Oxidation of Maltotetraose and Maltoheptaose

Maltotetraose (G4) and maltoheptaose (G7) were tested as potential oxidative substrates for the PQQ-ADH enzyme.

Each reaction was carried out in a total volume of 250 µl and consisted of:
12 mM G4 or 7 mM G7 (Sigma)
80 mM Na-phosphate buffer pH 7.0
4 mM $CaCl_2$ (Sigma)
360 µM PQQ (Fluka)
3.9 mM Phenazine methosulfate (Sigma)
0.1 mM 2,6-Dichlorophenolindophenol (Sigma)

Reactions were initiated by addition of 20 µl PQQ-ADH enzyme mixture and incubated for 12 hrs at 25° C. As a negative control samples were incubated with 20 µl water. Reactions were terminated by boiling for 2 min.

The reaction products were analyzed by FTMS and the products listed in Table 1 below were identified in PQQ-ADH treated samples.

TABLE 1

| G4 and G7 Reaction products identified by FTMS | | | |
|---|---|---|---|
| Substrate | Reaction product | Formula | Exact mass |
| G4 | Maltotetra-1-uronic acid | $C_{24}H_{42}O_{22}Na_1$ | 705.20442 |
|  | Sodium maltotetra-1-uronate | $C_{24}H_{41}O_{22}Na_2$ | 727.18643 |
|  | Maltotetra-6-uronic acid | $C_{24}H_{40}O_{22}Na_1$ | 703.19035 |
|  | Maltotetraose-6-aldehyde | $C_{24}H_{40}O_{21}Na_1$ | 687.19543 |
|  | Maltotetraose | $C_{24}H_{42}O_{21}Na_1$ | 689.21004 |
| G7 | Maltohepta-1-uronic acid | $C_{42}H_{72}O_{37}Na_1$ | 1191.36124 |
|  | Sodium maltohepta-1-uronate | $C_{42}H_{71}O_{37}Na_2$ | 1213.34291 |
|  | Maltohepta-6-aldehyde | $C_{42}H_{70}O_{36}Na_1$ | 1173.35176 |
|  | Maltoheptaose | $C_{42}H_{72}O_{36}Na_1$ | 1175.36657 |

The relative abundance of Maltotetraose-6-aldehyde indicates around 5% conversion when maltotetraose is applied as a substrate. A lower conversion (1-2%) to maltohepta-6-aldehyde is observed when maltoheptaose is used as a substrate.

It can be concluded from this example that PQQ-ADH can oxidize oligosaccharides at the C-1 and C-6 positions. The C-1-OH of the reducing end is oxidized to the carboxylic acid while modification at the C-6-OH yields the aldehyde as the major product and minor oxidation to the carboxylic acid.

Example 3

Oxidation of Starch by PQQ-ADH

Gelatinized wheat starch was tested as a substrate for PQQ-ADH, and the effects of $Fe^{2+}/Fe^{3+}$ addition were investigated.

In a total volume of 570 µl each reaction contained:
8 mg gelatinized wheat starch (Sigma)
90 mM Na-phosphate buffer pH 7.0
320 µM PQQ
Specified concentrations of $Fe^{2+}$ or $Fe^{3+}$
20 µg PQQ-ADH Samples were incubated at 40° C. for 24 hrs and the reaction terminated by boiling for 2 min. The pH of the samples were brought to 4.5 by addition of 125 µl 1 M sodium acetate. The starch polymer was degraded to monomers by addition of a mixture of α-amylase/glucoamylase, incubated at 70° C. for 3 hrs and terminated by boiling for 10 min. pH was adjusted to 7.0 with 5 M NaOH.

Figure 2:
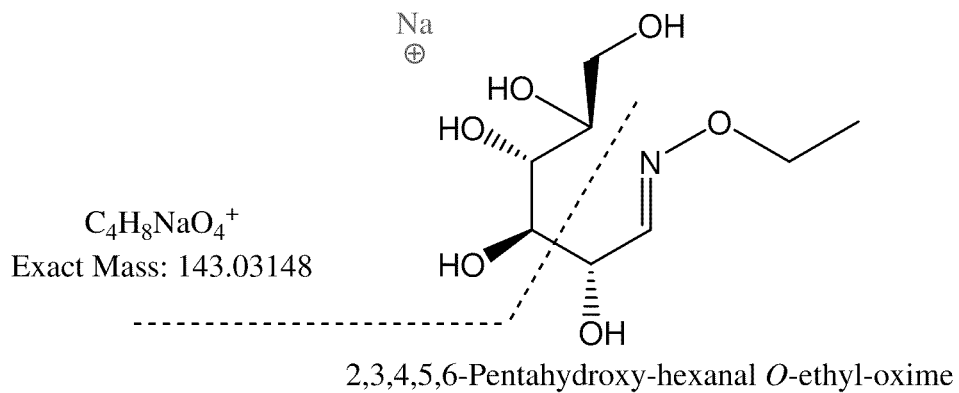
FIG. 2 illustrates the structure and fragment of glucose 1-ethyl oxime.
Figure 3:
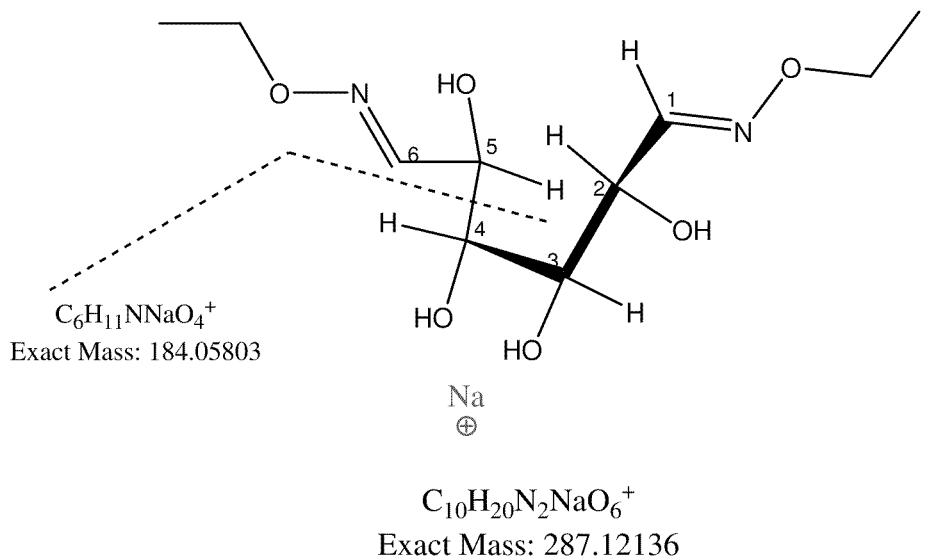
FIG. 3 illustrates the structure and fragment of glucose 1,6-bis(ethyl oxime).

40 µl 0.5 M Ethylhydroxylamine was added to derivatize molecules with aldehyde groups. Ethylhydroxylamine modification of C-1 and C-1/C-6 glucose derived aldehydes is shown in FIGS. 2 and 3. Samples were analyzed by FTMS.

Glucose 1,6-bis(ethyl oxime) represents glucosyl units in the starch polymer which have been oxidized to 6-aldehydes by PQQ-ADH. The ratio of glucose 1,6-bis(ethyl oxime) and glucose 1-ethyl oxime is a good measure of the ratio of the PQQ-ADH catalyzed conversion to C-6 glucosyl aldehyde within the starch polymer (Table 2).

TABLE 2

Oxidation of starch

| Sample | $Fe^{2+}$ (mM) | $Fe^{3+}$ (mM) | Conversion ratio, % |
|---|---|---|---|
| 1 | 0 | 0 | 2.3 |
| 2 | 0 | 0 | 2.2 |
| 3 | 0.02 | 0 | 5.3 |
| 4 | 0.2 | 0 | 5.2 |
| 5 | 0 | 0.1 | 6.6 |
| 6 | 0 | 1.0 | 3.4 |

It can be concluded from this example that PQQ-ADH can oxidize starch at the C-6 position of glucosyl units. Based on detection of the formed C-6 aldehyde a conversion rate of ~2% was obtained but this can be increased to ~5-6% with the addition of $Fe^{2+}$ or $Fe^{3+}$.

Example 4

Oxidation of Various Carbohydrates and Polysaccharides

A wide range of carbohydrates and polysaccharides were tested as potential oxidative substrates for the PQQ-ADH enzyme. Each reaction was carried out in a total volume of 250 µl and consisted of:
2% substrate
80 mM Na-phosphate buffer pH 7.0
4 mM $CaCl_2$
360 µM PQQ
3.9 mM Phenazine methosulfate
0.1 mM 2,6-Dichlorophenolindophenol (DCIP)

Reactions were initiated by addition of 20 µl PQQ-ADH enzyme mixture and incubated at 25° C. In the assay DCIP serves as the electron acceptor and oxidation of substrate was monitored by the reduction of DCIP to $DCIPH_2$ at 600 nm.

Oxidizing activity was observed for these substrates:
Glucose
Maltose
Maltotriose
Maltotetraose
Maltopentaose
Maltohexaose
Maltoheptaose
Amylose
Amylopectin
Glycogen
Butanol
Xylose
Trehalose
Anhydrofructose
Panose
Cellobiose
Cellopentaose
Melibiose
Arabinose
L-sorbose
Stachyose
Sucrose
α-cyclodextrin
β-cyclodextrin
γ-cyclodextrin
polydextrose
pectin
Pullulan
carrageenan
locust bean gum
guar gum
alginate
carboxymethyl cellulose
α-methyl glucose It can be concluded from this example that PQQ-ADH shows oxidizing activity on a broad range of substrates.

Example 5

Oxidation of Guar Gums

Four different guar gums with different viscosity profiles were treated with PQQ-ADH. The guar gums tested were Danisco products and these were Meyprodor 5, 50, 400 and Grindsted Guar 5000.

In a total volume of 700 ml each reaction contained:
5% Meyprodor 5, 1% Meyprodor 50, 0.5% Meyprodor 400 or 0.5% Grindsted Guar 5000 (all from Danisco A/S)
200 µM PQQ (Sigma)
0.1 µM FeCl3 (Sigma)
pH was adjusted to 7.0 with 1M HCl.
Reactions were initiated by addition of 4 mg PQQ-ADH enzyme mixture and incubated at 25° C. for 18 hrs.

The amount of negative charge in the guar products was investigated by Mütek particle charge detector where the guar gums are titrated with a cationic reagent (Table 3).

TABLE 3

Mütek analysis of PQQ-ADH treated guar gums

| Substrate | Control (ml) | PQQ-ADH treated (ml) |
|---|---|---|
| Grindsted Guar 5000 | 0.24 | 0.50 |
| Meyprodor 400 | 0.35 | 0.71 |
| Meyprodor 50 | 0.80 | 0.96 |
| Meyprodor 5 | 3.28 | 3.52 |

It can be concluded from this example that PQQ-ADH can oxidize guar gum and introduce negative charges into the polysaccharide.

Example 6

Oxidation of α- and β-cyclodextrin

α-cyclodextrin (α-CD) and β-cyclodextrin (β-CD) were tested as substrates for the PQQ-ADH enzyme. Each reaction was carried out in a total volume of 250 µl and consisted of:
15 mM α-CD or β-CD (Sigma)
50 mM Na-phosphate buffer pH 7.0
320 µM PQQ Reactions were initiated by addition of 20 µl PQQ-ADH enzyme mixture and incubated for 18 hrs at 40° C. As a negative control samples were incubated with 20 µl water. Reactions were terminated by boiling for 2 min.

The reaction products were analyzed by FTMS and the products listed in Table 4 were identified in PQQ-ADH treated samples.

TABLE 4

α-CD and β-CD reaction products identified by FTMS

| Substrate | Reaction product | Formula | Exact mass | Relative abundance |
|---|---|---|---|---|
| α-CD | α-cyclodextrin | $C_{36}H_{60}O_{30}Na_1$ | 995.30617 | 100 |
|  | α-cyclodextrin-6-aldehyde | $C_{36}H_{58}O_{30}Na_1$ | 993.28936 | 0.1 |
|  | α-cyclodextrin-6-acid | $C_{36}H_{58}O_{31}Na_1$ | 1009.28029 | 0.002 |
| β-CD | β-cyclodextrin | $C_{42}H_{70}O_{35}Na_1$ | 1157.35401 | 100 |
|  | β-cyclodextrin-6-aldehyde | $C_{42}H_{68}O_{35}Na_1$ | 1155.33957 | 0.2 |
|  | β-cyclodextrin-6-acid | $C_{42}H_{68}O_{36}Na_1$ | 1171.33214 | 0.003 |

It can be concluded from this example that PQQ-ADH can oxidize α-cyclodextrin and β-cyclodextrin at the C-6 position. Modification at the C-6-OH yields the aldehyde as the major product and a minor oxidation to the carboxylic acid is observed.

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by way of the following numbered paragraphs:

1. A method of oxidising a saccharide, by contacting the saccharide with an alcohol dehydrogenase (ADH) enzyme selected from a quinone redox cofactor-dependent ADH, a nicotinamide adenine dinucleotide (NAD$^+$) redox cofactor-dependent ADH, a nicotinamide adenine dinucleotide phosphate (NADP$^+$) redox cofactor-dependent ADH, and any combination thereof.
2. A method according to paragraph 1, wherein the alcohol dehydrogenase enzyme is in a purified form.
3. A method according to paragraph 1 or paragraph 2, wherein a redox cofactor is used with the alcohol dehydrogenase.
4. A method according to any one of paragraphs 1 to 3, wherein the alcohol dehydrogenase is selected from alcohol dehydrogenases in enzyme class EC 1.1.5.
5. A method according to paragraph 4, wherein the alcohol dehydrogenase is selected from alcohol dehydrogenases in enzyme class EC 1.1.5.2.
6. A method according to paragraph 5, wherein the alcohol dehydrogenase enzyme is selected from *Pseudogluconobacter saccharoketogenes* ADH (SEQ ID No 1), *Pseudogluconobacter saccharoketogenes* ADH (SEQ ID No 1A), *Escherichia coli* ADH (SEQ ID No. 5) and *Escherichia coli* ASD (SEQ ID No. 5a) or an alcohol dehydrogenase enzyme having at least 70% sequence identity to any thereof.
7. A method according to paragraph 6, wherein the alcohol dehydrogenase enzyme is selected from *Pseudogluconobacter saccharoketogenes* ADH (SEQ ID No 1), *Pseudogluconobacter saccharoketogenes* ADH (SEQ ID No 1A), *Escherichia coli* ADH (SEQ ID No. 5) and *Escherichia coli* ASD (SEQ ID No. 5a) or an alcohol dehydrogenase enzyme having at least 75% (such as at least 80%, or at least 85%, or at least 90%, or at least 95%, or at least 96%, or at least 97%, or at least 98% or or at least 99%) sequence identity to any thereof.
8. A method according to any one of paragraphs 1 to 3, wherein the alcohol dehydrogenase is selected from alcohol dehydrogenases in enzyme class EC 1.1.1.
9. A method according to paragraph 8, wherein the alcohol dehydrogenase is selected from alcohol dehydrogenases in enzyme classes EC 1.1.1.1 and EC 1.1.1.2.
10. A method according to paragraph 8 or paragraph 9, wherein the alcohol dehydrogenase enzyme is selected from *Lactobacillus kefir* ADH (SEQ ID No 2), *Lactobacillus kefir* ADH (SEQ ID No 2a), *Saccharomyces cerevisiae* ADH (SEQ ID No 3) or *Thermoanaerobium brockii* ADH (SEQ ID No 4) or an alcohol dehydrogenase enzyme having at least 70% sequence identity to any thereof; preferably wherein the alcohol dehydrogenase enzyme is selected from *Lactobacillus kefir* ADH (SEQ ID No 2), *Lactobacillus kefir* ADH (SEQ ID No 2a), *Saccharomyces cerevisiae* ADH (SEQ ID No 3) or *Thermoanaerobium brockii* ADH (SEQ ID No 4) or an alcohol dehydrogenase enzyme having at least 75% (such as at least 80%, or at least 85%, or at least 90%, or at least 95%, or at least 96%, or at least 97%, or at least 98% or at least 99%) sequence identity to any thereof.
11. A method according to any of paragraphs 3 to 7, wherein the redox cofactor is a quinone cofactor.
12. A method according to paragraph 11, wherein the quinone cofactor is selected from pyrroloquinoline quinone (PQQ), tryptophyl tryptophanquinone (TTQ), topaquinone (TPQ), and lysine tyrosylquinone (LTQ).
13. A method according to paragraph 12, wherein the redox cofactor is pyrroloquinoline quinone (PQQ).
14. A method according to paragraph 13, wherein the PQQ is derived from green tea extract.
15. A method according to paragraph 13 or paragraph 14, wherein the PQQ is present in a concentration of about 0.01 to about 1000 ppm by weight.
16. A method according to paragraph 15, wherein the PQQ is present in a concentration of about 0.2 to about 100 ppm by weight.
17. A method according to any one of paragraphs 11 to 16, wherein a metal ion is used with the quinone cofactor.

18. A method according to paragraph 17, wherein the metal ion is a $Fe^{2+}$ or $Fe^{3+}$ ion, or a combination thereof.
19. A method according to any of paragraphs 3, 8, 9 or 10, wherein the redox cofactor is selected from $NAD^+$ and $NADP^+$.
20. A method according to paragraph 19, wherein the $NAD^+$ or $NADP^+$ is present in a concentration of about 0.01 to about 5000 ppm by weight.
21. A method according to paragraph 20, wherein the $NAD^+$ or $NADP^+$ is present in a concentration of about 0.10 to about 1000 ppm by weight.
22. A method according to any one of paragraphs 1 to 21, wherein the concentration of alcohol dehydrogenase used is at least about 0.05 ppm by weight.
23. A method according to any one of paragraphs 1 to 22, comprising oxidation of at least 2% of the primary alcohol groups of the saccharide to aldehyde groups.
24. A method according to paragraph 23, comprising oxidation of at least 6% of the primary alcohol groups of the saccharide to aldehyde groups.
25. A method according to any one of paragraphs 1 to 24, wherein the saccharide is a polysaccharide comprising hexose moieties.
26. A method according to paragraph 25, wherein the hexose moieties of the polysaccharide are glucose moieties.
27. A method according to paragraph 25 or paragraph 26, comprising selective oxidation of alcohol groups at the C-6 position of the hexose moieties of the polysaccharide.
28. A method according to any one of paragraphs 1 to 24, wherein the saccharide is a polysaccharide comprising pentose moieties.
29. A method according to paragraph 28, wherein the pentose moieties of the polysaccharide are arabinose or xylose moieties.
30. A method according to paragraph 28 or paragraph 29, comprising selective oxidation of alcohol groups at the C-5 position of the pentose moieties of the polysaccharide.
31. A method according to any one of paragraphs 1 to 24, wherein the saccharide is a disaccharide.
32. A method according to paragraph 31, wherein the disaccharide is selected from lactose, maltose, cellobiose, sucrose, trehalose isomaltulose and trehalulose.
33. A method according to any one of paragraphs 1 to 24, wherein the saccharide is an oligosaccharide
34. A method according to paragraph 33, wherein the oligosaccharide is a chain oligosaccharide.
35. A method according to paragraph 34, wherein the polysaccharide is selected from maltotriose, maltotetraose, maltopentaose, maltohexaose, maltoheptaose, cellobiose, cellotriose, cellotetraose, cellopentaose, cellohexaose, celloheptaose, a fructo-oligosaccharide, a mannanoligosaccharide; and an isomaltooligosaccharide, a galactooligosaccharide and a xylooligosaccharide.
36. A method according to paragraph 33, wherein the oligosaccharide is a cyclic oligosaccharide.
37. A method according to paragraph 36, wherein the cyclic oligosaccharide is a cyclodextrin selected from α-cyclodextrin, β-cyclodextrin and γ-cyclodextrin.
38. A method according to any one of paragraphs 1 to 24, wherein the saccharide is a polysaccharide comprising at least 40 monosaccharide units.
39. A method according to paragraph 38, wherein the polysaccharide comprises at least 1000 monosaccharide units.
40. A method according to paragraph 38 or paragraph 39, wherein the polysaccharide is selected from starch, amylose, amylopectin, glycogen, arabinoxylan, a β-glucan, cellulose or a derivative thereof, alginic acid or a salt or derivative thereof, polydextrose, pectin, pullulan, carrageenan, locust bean gum and guar gum.
41. A method according to paragraph 40, wherein the polysaccharide is starch.
42. An oxidised saccharide obtainable by the method of any one of paragraphs 1 to 41.
43. A product containing an oxidised saccharide obtainable by the method of any one of paragraphs 1 to 41.
44. A product according to paragraph 43, selected from a food product and a paper product.
45. A product according to paragraph 44, which is a food product selected from dough and a baked product prepared from dough.
46. Use of an oxidised saccharide obtainable by the method of any one of paragraphs 1 to 41 in the manufacture of food products or paper products.
47. Use of an alcohol dehydrogenase as defined in any one of paragraphs 1 to 10 in the manufacture of paper products.
48. Use of an alcohol dehydrogenase selected from a quinone redox cofactor-dependent ADH, a nicotinamide adenine dinucleotide ($NAD^+$) redox cofactor-dependent ADH, a nicotinamide adenine dinucleotide phosphate ($NADP^+$) redox cofactor-dependent ADH, and any combinations thereof for oxidising saccharides and/or for preparing food or paper products.
49. An amino acid sequence comprising SEQ ID No. 1A or an amino acid sequence having at least 75% amino acid sequence identity therewith but not SEQ ID No. 1.
50. An amino acid sequence according to paragraph 49 comprising SEQ ID No. 1A or an amino acid sequence having at least 80%, at least 85%, at least 90%, at least 95%, at least 96%, at least 97%, at least 98% or at least 99%, amino acid sequence identity therewith.
51. A nucleotide sequence encoding the amino acid sequence of paragraph 49 or paragraph 50.
52. A vector comprising the nucleotide sequence of paragraph 51.
53. A host transformed with the nucleotide sequence of paragraph 51 or the vector of paragraph 52.
54. A host according to paragraph 53 wherein the host is selected from a bacterial host, a fungal host or a yeast host.
55. A method comprising expressing the nucleotide sequence of paragraph 51 or the vector of paragraph 52.
56. An amino acid sequence comprising SEQ ID No. 2A or an amino acid sequence having at least 75% amino acid sequence identity therewith but not SEQ ID No. 2.
57. An amino acid sequence according to paragraph 56 comprising SEQ ID No. 2A or an amino acid sequence having at least 80%, at least 85%, at least 90%, at least 95%, at least 96%, at least 97%, at least 98% or at least 99%, amino acid sequence identity therewith.
58. A nucleotide sequence encoding the amino acid sequence of paragraph 56 or paragraph 57.
59. A vector comprising the nucleotide sequence of paragraph 58.
60. A host transformed with the nucleotide sequence of paragraph 58 or the vector of paragraph 59.
61. A host according to paragraph 60 wherein the host is selected from a bacterial host, a fungal host or a yeast host.

62. A method comprising expressing the nucleotide sequence of paragraph 58 or the vector of paragraph 59.
63. An amino acid sequence comprising SEQ ID No. 5A or an amino acid sequence having at least 75% amino acid sequence identity therewith but not SEQ ID No. 5.
64. An amino acid sequence according to paragraph 63 comprising SEQ ID No. 2A or an amino acid sequence having at least 80%, at least 85%, at least 90%, at least 95%, at least 96%, at least 97%, at least 98% or at least 99%, amino acid sequence identity therewith.
65. A nucleotide sequence encoding the amino acid sequence of paragraph 63 or paragraph 64.
66. A vector comprising the nucleotide sequence of paragraph 65.
67. A host transformed with the nucleotide sequence of paragraph 65 or the vector of paragraph 66.
68. A host according to paragraph 67 wherein the host is selected from a bacterial host, a fungal host or a yeast host.
69. A method comprising expressing the nucleotide sequence of paragraph 65 or the vector of paragraph 66.
70. A method according to paragraph 1 or any claim dependent thereon or a use according to paragraph 48 wherein said saccharide is selected from the group consisting of: Glucose, Maltose, Maltotriose, Maltotetraose, Maltopentaose, Maltohexaose, Maltoheptaose, Amylose, Amylopectin, Glycogen, Butanol, Xylose, Trehalose, Anhydrofructose, Panose, Cellobiose, Cellopentaose, Melibiose, Arabinose, L-sorbose, Stachyose, Sucrose, α-cyclodextrin, β-cyclodextrin, γ-cyclodextrin, polydextrose, pectin, Pullulan, carrageenan, locust bean gum, guar gum, alginate, carboxymethyl cellulose, α-methyl glucose, and combinations thereof.
71. A method or a saccharide or a product or a use substantially as described herein and with reference to the accompanying figures.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

An amino acid sequence or a nucleotide sequence or a vector or a host or a method substantially as described herein and with reference to the accompanying figures.

SEQUENCE LISTINGS

SEQ ID No. 1

*Pseudogluconobacter saccharoketogenes* alcohol dehydrogenase (PsADH)
EC number 1.1.5.2
(Acc BAB62258)

```
  1 mrfeylrqnv vglalstali aslsgpafaq hdanaaaeps kagqsaienf qpvtaddlag
 61 knpanwpilr gnyqgwgysp ldqinkdnvg dlqlvwsrtm epgsnegaai ayngviflgn
121 tndviqaidg ktgsliweyr rklpsaskfi nslgaakrsi alfgdkvyfv swdnfvvald
181 aktgklawet nrgqgveegv anssgpivvd gvviagstcq fsgfgcyvtg tdaesgeelw
241 rntfiprpge egddtwggap yenrwmtgaw gqitydpeld lvyygstgag pasevqrgte
301 ggtlagtntr favkpktgev vwkhqtlprd nwdsectfem mvvstsvnpd akadgmmsvg
361 anvprgetrk vltgvpcktg vawqfdaktg dyfwskatve qnsiasiddt glvtvnedmi
421 lkepgktyny cptflggrdw psagylpksn lyviplsnac ydvmarttea tpadvyntda
481 tlvlapgktn mgrvdaidla tgetkwsyet raalydpvlt tggdlvfvgg idrdfralda
541 esgkevwstr lpgavsgytt sysidgrqyv avvsggslgg ptfgpttpdv dsasgangiy
601 vfalpekk
```

SEQ ID No. 1A (which can be referred to as SEQ ID No. 7)
*Pseudogluconobacter saccharoketogenes* alcohol dehydrogenase (PsADH)
EC number 1.1.5.2
(Acc BAB62258)

```
aeps kagqsaienf qpvtaddlag
knpanwpilr gnyqgwgysp ldqinkdnvg dlqlvwsrtm epgsnegaai ayngviflgn
tndviqaidg ktgsliweyr rklpsaskfi nslgaakrsi alfgdkvyfv swdnfvvald
aktgklawet nrgqgveegv anssgpivvd gvviagstcq fsgfgcyvtg tdaesgeelw
rntfiprpge egddtwggap yenrwmtgaw gqitydpeld lvyygstgag pasevqrgte
ggtlagtntr favkpktgev vwkhqtlprd nwdsectfem mvvstsvnpd akadgmmsvg
anvprgetrk vltgvpcktg vawqfdaktg dyfwskatve qnsiasiddt glvtvnedmi
lkepgktyny cptflggrdw psagylpksn lyviplsnac ydvmarttea tpadvyntda
tlvlapgktn mgrvdaidla tgetkwsyet raalydpvlt tggdlvfvgg idrdfralda
esgkevwstr lpgavsgytt sysidgrqyv avvsggslgg ptfgpttpdv dsasgangiy
vfalpekk
```

SEQ ID No. 2

*Lactobacillus kefir* ADH (LkADH) (05643 Sigma)
EC Number 1.1.1.2
(Acc AAP94029)

```
  1 mtdrlkgkva ivtggtlgig laiadkfvee gakvvitgrh advgekaaks iggtdvirfv
 61 qhdasdeagw tklfdtteea fgpvttvvnn agiavsksve dttteewrkl lsvnldgvff
121 gtrlgiqrmk nkglgasiin mssiegfvgd ptlgaynask gavrimsksa aldcalkdyd
181 vrvntvhpgy iktplvddle gaeemmsqrt ktpmghigep ndiawicvyl asdeskfatg
241 aefvvdggyt aq
```

SEQ ID No. 2a (which can be referred to as SEQ ID No. 8)

```
dkfvee gakvvitgrh advgekaaks iggtdvirfv
qhdasdeagw tklfdtteea fgpvttvvnn agiavsksve dttteewrkl lsvnldgvff
gtrlgiqrmk nkglgasiin mssiegfvgd ptlgaynask gavrimsksa aldcalkdyd
vrvntvhpgy iktplvddle gaeemmsqrt ktpmghigep ndiawicvyl asdeskfatg
aefvvdggyt aq
```

SEQUENCE LISTINGS

SEQ ID No. 3

*Saccharomyces cerevisiae* ADH (ScADH) (A 3263 Sigma)
EC Number 1.1.1.1
(Acc CAA91578)

```
  1 msaatvgkpi kciaavayda kkplsveeit vdapkahevr ikieytavch tdaytlsgsd
 61 peglfpcvlg hegagivesv gddvitvkpg dhvialytae cgkckfctsg ktnlcgavra
121 tqgkgvmpdg ttrfhnakge diyhfmgcst fseytvvadv svvaidpkap ldaacllgcg
181 vttgfgaalk tanvqkgdtv avfgcgtvgl sviqgaklrg askiiaidin nkkkqycsqf
241 gatdfvnpke dlakdqtive kliemtdggl dftfdctgnt kimrdaleac hkgwgqsiii
301 gvaaageeis trpfqlvtgr vwkgsafggi kgrsemggli kdyqkgalkv eefithrrpf
361 keinqafedl hngdclrtvl ksdeik
```

SEQ ID No. 4

*Thermoanaerobium brockii* ADH (TbADH) (A8435 Sigma)
EC Number 1.1.1.2
(Acc CAA46053)

```
  1 mkgfamlsig kvgwiekekp apgpfdaivr plavapctsd ihtvfegaig erhnmilghe
 61 avgevvevgs evkdfkpgdr vvvpaitpdw rtsevqrgyh qhsggmlagw kfsnvkdgvf
121 geffhvndad mnlahlpkei pleaavmipd mmttgfhgae ladielgatv avlgigpvgl
181 mavagaklrg agriiavgsr pvcvdaakyy gatdivnykd gpiesqimnl tegkgvdaai
241 iaggnadima tavkivkpgg tianvnyfge gevlpvprle wgcgmahkti kgglcpggrl
301 rmerlidlvf ykrvdpsklv thvfrgfdni ekafmlmkdk pkdlikpvvi la
```

SEQ ID No. 5

*Escherichia coli* ADH (EcADH) (Acc NP_415358)
EC Number 1.1.5.2

```
  1 mhrqsfflvp liclssalwa apatvnvevl qdkldhpwal aflpdnhgml itlrggelrh
 61 wqagkglsap lsgvpdvwah gqgglldvvl apdfaqsrri wlsysevgdd gkagtavgyg
121 rlsddlskvt dfrtvfrqmp klstgnhfgg rlvfdgkgyl fialgennqr ptaqdldklq
181 gklvrltdqg eipddnpfik esgaraeiws ygirnpqgma mnpwsnalwl nehgprggde
241 inipqkgkny gwplatwgin ysgfkipeak geivagteqp vfywkdspav sgmafynsdk
301 fpqwqqklfi galkdkdviv msvngdkvte dgriltdrgq rirdvrtgpd gylyvltdes
361 sgellkvspr n
```

SEQ ID No. 5a (which can be referred to as SEQ ID No. 9)

```
apatvnvevl qdkldhpwal aflpdnhgml itlrggelrh
wqagkglsap lsgvpdvwah gqgglldvvl apdfaqsrri wlsysevgdd gkagtavgyg
rlsddlskvt dfrtvfrqmp klstgnhfgg rlvfdgkgyl fialgennqr ptaqdldklq
gklvrltdqg eipddnpfik esgaraeiws ygirnpqgma mnpwsnalwl nehgprggde
inipqkgkny gwplatwgin ysgfkipeak geivagteqp vfywkdspav sgmafynsdk
fpqwqqklfi galkdkdviv msvngdkvte dgriltdrgq rirdvrtgpd gylyvltdes
sgellkvspr n
```

SEQ ID No. 6

DNA sequence of the codon optimized PQQ-ADH gene

*ggtaccacaagtttgtacaaaaaagcaggctt*catgagattcgagtacctgcgccagaacgttgtcggtttggctctttcta
ccgccctgatcgcatccctcagcgccctgcttttgcccaacacgacgctaatgctgccgccgaaccatcaaaggcagga
cagtcggcaattgagaacttccaaccggtgactgctgacgatttggccggtaaaaaccctgcaaattggcccatccttcgtg
gcaactaccagggatggggtatagtccactggaccagattacaaggataatgtcggtgattcgagctcgtttggtctcg
gacaatggaaccgggaagcaatgagggcgctgctatcgcctataacggtgtgattttctgggcaacacgaatgacgttat
ccaagccattgatgaaaaaccggttcccttatctgggaatacagacgaaagctcccctcagcatctaaattcattaactcgt
tgggggctgctaagaggtccatcgccctgtttggcgacaaggtctacttcgtgagttgggataatttgttgtcgcccttgacg
caaagactggaaaactggcttgggagacaaacagaggtcaaggtgttgaggaaggcgtggccaactctagcggacctat
tgttgtcgatggcgtcgtgatcgcagggtccacctgccagttctcaggttttggctgttatgtgactggaacggacgctgagt
cgggtgaagaattgtggcgcaatacctttcattccacgtccggagaggaaggtgacgatacatgggggcggagcaccta
cgagaaccggtggatgacgggtgcctggggccaaatcacctatgaccagaacttgatctcgtttactatggttctactggg
gctggacctgcctccgaggtccagagaggtacagaaggcggcaccctggctggaactaatacacgctttgccgtgaagc
ccaaaacgggagaggttgtctggaaacatcaaaccttgccgagagacaactgggatagcgagtgcactttcgaaatgatg
gttgtctcaaccagtgtgaatccagacgctaaggcagatggtatgatgtctgttggggcaacgtgcctaggggcgagaca
cgtaaggttctcacgggtgtcccgtgtaaaactggcgtggcttggcagtttgatgcaaagacgggagactacttctggtcga
aagccaccgtcgaacaaaactccatcgctagcattgacgataccggtctggttacagtcaatgaggacatgattttgaaaga
acccggcaagacttacaactattgcccaacattccttggagggcgagattggccttctgccggttacctgccgaagtcaaat
ttgtatgtgatcccactctccaacgcatgttacgatgttatgctagaaccactgaggccacgcccgctgacgtctataacac
cgatgccacactggtgcttgcacctggcaagacgaatatgggacggcgttgacgctatcgatctcgccaccggtgaaacaa
aatggtcgtacgagacaagagctgcactgtatgacccggtcttgaccactggcggagatcttgtttttgtgggtggaattgac
cgtgacttccgggctctggatgccgagagcggggaaagaagtctggtctacaaggttgccaggtgcagtgtccggctacac
cacgtcatacagtattgatggcagacagtatgttgccgtcgtttctggtggtagcctcggcggacctaccttggaccgacta
cacccgacgtggattccgcttcgggagcaaacgggatctacgtctcttgccctgcctgaaaagaagta*ataaacccagcttt*
*cttgtacaaagtggtgagctc*

The invention claimed is:

1. A method of oxidising a saccharide, comprising contacting the saccharide with a quinone redox cofactor-dependent alcohol dehydrogenase (ADH) enzyme wherein the quinone redox cofactor-dependent ADH is a recombinantly produced polypeptide having alcohol dehydrogenase activity comprising amino acid sequence SEQ ID No. 7 or an amino acid sequence having at least 90% amino acid sequence identity therewith, but not SEQ ID NO: 1.

2. A method according to claim 1, wherein the alcohol dehydrogenase enzyme is in a purified form.

3. A method according to claim 1, wherein a redox cofactor is used with the alcohol dehydrogenase.

4. A method according to claim 1, wherein the alcohol dehydrogenase is an alcohol dehydrogenases enzyme of class EC 1.1.5.

5. A method according to claim 1, wherein the alcohol dehydrogenase is an alcohol dehydrogenases enzyme of class EC 1.1.5.2.

6. A method according to claim 1, wherein the alcohol dehydrogenase enzyme is selected from the group consisting of *Pseudogluconobacter saccharoketogenes* ADH (SEQ ID No 7) and an alcohol dehydrogenase enzyme having at least 90% sequence identity thereto.

7. A method according to claim 1, wherein the alcohol dehydrogenase enzyme is a recombinantly produced polypeptide having alcohol dehydrogenase activity comprising an amino acid sequence at least 90%, at least 95%, at least 96%, at least 97%, at least 98% or at least 99%, amino acid sequence identity with SEQ ID No. 7.

8. A method according to claim 7, wherein the redox cofactor is a quinone cofactor.

9. A method according to claim 8, wherein the redox cofactor is a quinone cofactor selected from the group consisting of pyrroloquinoline quinone (PQQ), tryptophyl tryptophan-quinone (TTQ), topaquinone (TPQ), and lysine tyrosylquinone (LTQ).

10. A method according to claim 9, wherein the redox cofactor is pyrroloquinoline quinone (PQQ).

11. A method according to claim 10, wherein the redox cofactor is PQQ derived from green tea extract.

12. A method according to claim 10, wherein the redox cofactor is PQQ and is present in a concentration of about 0.01 to about 1000 ppm by weight.

13. A method according to claim 10, wherein the redox cofactor is PQQ and is present in a concentration of about 0.2 to about 100 ppm by weight.

14. A method according to claim 8, wherein a metal ion is used with the quinone cofactor.

15. A method according to claim 14, wherein the metal ion is a $Fe^{2+}$ or $Fe^{3+}$ ion, or a combination thereof.

16. A method according to claim 1, wherein the concentration of alcohol dehydrogenase used is at least about 0.05 ppm by weight.

17. A method according to claim 1, comprising oxidation of at least 2% of the primary alcohol groups of the saccharide to aldehyde groups.

18. A method according to claim 1, comprising oxidation of at least 6% of the primary alcohol groups of the saccharide to aldehyde groups.

19. A method according to claim 1, wherein the saccharide is a polysaccharide comprising hexose moieties.

20. A method according to claim 19, wherein the saccharide is a polysaccharide comprising hexose moieties and wherein the hexose moieties of the polysaccharide are glucose moieties.

21. A method according to claim 19, wherein the saccharide is a polysaccharide comprising hexose moieties, comprising selective oxidation of alcohol groups at the C-6 position of the hexose moieties of the polysaccharide.

22. A method according to claim 1, wherein the saccharide is a polysaccharide comprising pentose moieties.

23. A method according to claim 22, wherein the saccharide is a polysaccharide comprising pentose moieties and wherein the pentose moieties of the polysaccharide are arabinose or xylose moieties.

24. A method according to claim 22, wherein the saccharide is a polysaccharide comprising pentose moieties, comprising selective oxidation of alcohol groups at the C-5 position of the pentose moieties of the polysaccharide.

25. A method according to claim 1, wherein the saccharide is a disaccharide.

26. A method according to claim 25, wherein the saccharide is a disaccharide and wherein the disaccharide is selected from the group consisting of lactose, maltose, cellobiose, sucrose, trehalose isomaltulose and trehalulose.

27. A method according to claim 25, wherein the saccharide is a disaccharide and wherein the saccharide is an oligosaccharide.

28. A method according to claim 27, wherein the saccharide is an oligosaccharide and wherein the oligosaccharide is a chain oligosaccharide.

29. A method according to claim 1, wherein the saccharide is selected from the group consisting of maltotriose, maltotetraose, maltopentaose, maltohexaose, maltoheptaose, cellobiose, cellotriose, cellotetraose, cellopentaose, cellohexaose, celloheptaose, a fructo-oligosaccharide, a mannanoligosaccharide; and an isomaltooligosaccharide, a galactooligosaccharide and a xylooligosaccharide.

30. A method according to claim 27, wherein the saccharide is a cyclic oligosaccharide.

31. A method according to claim 30, wherein the saccharide is a cyclodextrin selected from the group consisting of α-cyclodextrin, β-cyclodextrin and γ-cyclodextrin.

32. A method according to claim 1, wherein the saccharide is a polysaccharide comprising at least 40 monosaccharide units.

33. A method according to claim 1, wherein the saccharide is a polysaccharide comprising at least 1000 monosaccharide units.

34. A method according to claim 1, wherein the saccharide is a polysaccharide selected from the group consisting of starch, amylose, amylopectin, glycogen, arabinoxylan, a β-glucan, cellulose or a derivative thereof, alginic acid or a salt or derivative thereof, polydextrose, pectin, pullulan, carrageenan, locust bean gum and guar gum.

35. A method according to claim 1, wherein the saccharide is starch.

36. A recombinantly produced polypeptide having alcohol dehydrogenase activity comprising amino acid sequence SEQ ID No. 7 or an amino acid sequence having at least 90% amino acid sequence identity therewith but not SEQ ID No. 1.

37. The recombinantly produced polypeptide having alcohol dehydrogenase activity according to claim 36 comprising amino acid sequence SEQ ID No. 7 or an amino acid sequence having at least 95%, at least 96%, at least 97%, at least 98% or at least 99%, amino acid sequence identity therewith.

38. A method according to claim 1 wherein said saccharide is selected from the group consisting of: Glucose, Maltose, Maltotriose, Maltotetraose, Maltopentaose, Maltohexaose, Maltoheptaose, Amylose, Amylopectin, Glycogen, Butanol, Xylose, Trehalose, Anhydrofructose, Panose, Cellobiose, Cellopentaose, Melibiose, Arabinose, L-sorbose, Stachyose, Sucrose, α-cyclodextrin, β-cyclodextrin, γ-cyclodextrin, polydextrose, pectin, Pullulan, carrageenan, locust bean gum, guar gum, alginate, carboxymethyl cellulose, α-methyl glucose, and combinations thereof.

39. The recombinantly produced polypeptide having alcohol dehydrogenase activity according to claim 37, wherein said amino acid sequence has at least 95% identity with SEQ ID No. 7.

40. The recombinantly produced polypeptide having alcohol dehydrogenase activity according to claim 37, wherein said amino acid sequence has at least 96% identity with SEQ ID No. 7.

41. The recombinantly produced polypeptide having alcohol dehydrogenase activity according to claim 37, wherein said amino acid sequence has at least 97% identity with SEQ ID No. 7.

42. The recombinantly produced polypeptide having alcohol dehydrogenase activity according to claim 37, wherein said amino acid sequence has at least 98% identity with SEQ ID No. 7.

43. The recombinantly produced polypeptide having alcohol dehydrogenase activity according to claim 37, wherein said amino acid sequence has at least 99% identity with SEQ ID No. 7.

* * * * *